(12) United States Patent
Blanchard et al.

(10) Patent No.: US 12,137,987 B2
(45) Date of Patent: Nov. 12, 2024

(54) ULTRASOUND SYSTEMS AND METHODS FOR SUSTAINED SPATIAL ATTENTION

(71) Applicant: Bard Access Systems, Inc., Salt Lake City, UT (US)

(72) Inventors: Daniel B. Blanchard, Bountiful, UT (US); Zachary S. Davis, Sandy, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 17 days.

(21) Appl. No.: 17/491,308

(22) Filed: Sep. 30, 2021

(65) Prior Publication Data
US 2022/0104886 A1    Apr. 7, 2022

Related U.S. Application Data

(60) Provisional application No. 63/086,971, filed on Oct. 2, 2020.

(51) Int. Cl.
*A61B 34/20*         (2016.01)
*A61B 8/00*          (2006.01)
(Continued)

(52) U.S. Cl.
CPC .............. *A61B 34/20* (2016.02); *A61B 8/0841* (2013.01); *A61B 8/4254* (2013.01);
(Continued)

(58) Field of Classification Search
CPC ........ A61B 34/20; A61B 8/4254; A61B 8/463; A61B 17/3403; A61B 2017/3405;
(Continued)

(56) References Cited

U.S. PATENT DOCUMENTS

| 5,148,809 A | 9/1992 | Biegeleisen-Knight et al. |
| 5,181,513 A | 1/1993 | Touboul et al. |

(Continued)

FOREIGN PATENT DOCUMENTS

| AU | 2006201646 A1 | 11/2006 |
| CN | 114129137 B | 9/2022 |

(Continued)

OTHER PUBLICATIONS

Stolka, P.J., et al., (2014). Needle Guidance Using Handheld Stereo Vision and Projection for Ultrasound-Based Interventions. In: Golland, P., Hata, N., Barillot, C., Hornegger, J., Howe, R. (eds) Medical Image Computing and Computer-Assisted Intervention—MICCAI 2014. MICCAI 2014. (Year: 2014).*

(Continued)

*Primary Examiner* — Colin T. Sakamoto
*Assistant Examiner* — Tommy T Ly
(74) *Attorney, Agent, or Firm* — Rutan & Tucker LLP

(57) ABSTRACT

Disclosed herein are ultrasound systems and methods for sustained spatial attention. For example, an ultrasound system can include a console and an ultrasound probe. A display of the console can be configured to display ultrasound images and one or more still or moving images of a procedural field. The ultrasound probe can include a camera integrated into the ultrasound probe for recording the one-or-more still or moving images of the procedural field with a depth of field including a distal end of a probe head and a field of view including a spatial region about the probe head. With the one-or-more still or moving images displayed along with the ultrasound images, a clinician need not switch his or her spatial attention between spatial regions such as the procedural field and the display quite as frequently as with existing ultrasound systems, thereby sustaining spatial attention in one or more spatial regions.

17 Claims, 10 Drawing Sheets

(51) Int. Cl.
*A61B 8/08* (2006.01)
*A61B 17/34* (2006.01)

(52) U.S. Cl.
CPC ............ *A61B 8/4488* (2013.01); *A61B 8/463* (2013.01); *A61B 17/3403* (2013.01); *A61B 2017/3405* (2013.01); *A61B 2034/2057* (2016.02); *A61B 2034/2065* (2016.02)

(58) Field of Classification Search
CPC .... A61B 2034/2057; A61B 2034/2065; A61B 90/13; A61B 6/08; A61B 8/0841; A61B 2090/378
See application file for complete search history.

(56) References Cited

U.S. PATENT DOCUMENTS

| | | | |
|---|---|---|---|
| 5,325,293 | A | 6/1994 | Dorne |
| 5,441,052 | A | 8/1995 | Miyajima |
| 5,549,554 | A | 8/1996 | Miraki |
| 5,573,529 | A | 11/1996 | Haak et al. |
| 5,775,322 | A | 7/1998 | Silverstein et al. |
| 5,879,297 | A | 3/1999 | Haynor et al. |
| 5,908,387 | A | 6/1999 | LeFree et al. |
| 5,967,984 | A | 10/1999 | Chu et al. |
| 5,970,119 | A | 10/1999 | Hofmann |
| 6,004,270 | A | 12/1999 | Urbano et al. |
| 6,019,724 | A | 2/2000 | Gronningsaeter et al. |
| 6,068,599 | A | 5/2000 | Saito et al. |
| 6,074,367 | A | 6/2000 | Hubbell |
| 6,129,668 | A | 10/2000 | Haynor et al. |
| 6,132,379 | A | 10/2000 | Patacsil et al. |
| 6,216,028 | B1 | 4/2001 | Haynor et al. |
| 6,233,476 | B1 | 5/2001 | Strommer et al. |
| 6,245,018 | B1 | 6/2001 | Lee |
| 6,263,230 | B1 | 7/2001 | Haynor et al. |
| 6,375,615 | B1 | 4/2002 | Flaherty et al. |
| 6,436,043 | B2 | 8/2002 | Bonnefous |
| 6,498,942 | B1 | 12/2002 | Esenaliev et al. |
| 6,503,205 | B2 | 1/2003 | Manor et al. |
| 6,508,769 | B2 | 1/2003 | Bonnefous |
| 6,511,458 | B2 | 1/2003 | Milo et al. |
| 6,524,249 | B2 | 2/2003 | Moehring et al. |
| 6,543,642 | B1 | 4/2003 | Milliorn |
| 6,554,771 | B1 | 4/2003 | Buil et al. |
| 6,592,520 | B1 | 7/2003 | Peszynski et al. |
| 6,592,565 | B2 | 7/2003 | Twardowski |
| 6,601,705 | B2 | 8/2003 | Molina et al. |
| 6,612,992 | B1 | 9/2003 | Hossack et al. |
| 6,613,002 | B1 | 9/2003 | Clark et al. |
| 6,623,431 | B1 | 9/2003 | Sakuma et al. |
| 6,641,538 | B2 | 11/2003 | Nakaya et al. |
| 6,647,135 | B2 | 11/2003 | Bonnefous |
| 6,687,386 | B1 | 2/2004 | Ito et al. |
| 6,749,569 | B1 | 6/2004 | Pellegretti |
| 6,754,608 | B2 | 6/2004 | Svanerudh et al. |
| 6,755,789 | B2 | 6/2004 | Stringer et al. |
| 6,840,379 | B2 | 1/2005 | Franks-Farah et al. |
| 6,857,196 | B2 | 2/2005 | Dalrymple |
| 6,979,294 | B1 | 12/2005 | Selzer et al. |
| 7,074,187 | B2 | 7/2006 | Selzer et al. |
| 7,244,234 | B2 | 7/2007 | Ridley et al. |
| 7,359,554 | B2 | 4/2008 | Klingensmith et al. |
| 7,534,209 | B2 | 5/2009 | Abend et al. |
| 7,599,730 | B2 | 10/2009 | Hunter et al. |
| 7,637,870 | B2 | 12/2009 | Flaherty et al. |
| 7,681,579 | B2 | 3/2010 | Schwartz |
| 7,691,061 | B2 | 4/2010 | Hirota |
| 7,699,779 | B2 | 4/2010 | Sasaki et al. |
| 7,720,520 | B2 | 5/2010 | Willis |
| 7,727,153 | B2 | 6/2010 | Fritz et al. |
| 7,734,326 | B2 | 6/2010 | Pedain et al. |
| 7,831,449 | B2 | 11/2010 | Ying et al. |
| 7,905,837 | B2 | 3/2011 | Suzuki |
| 7,925,327 | B2 | 4/2011 | Weese |
| 7,927,278 | B2 | 4/2011 | Selzer et al. |
| 8,014,848 | B2 | 9/2011 | Birkenbach et al. |
| 8,050,523 | B2 | 11/2011 | Younge et al. |
| 8,060,181 | B2 | 11/2011 | Rodriguez Ponce et al. |
| 8,068,581 | B2 | 11/2011 | Boese et al. |
| 8,075,488 | B2 | 12/2011 | Burton |
| 8,090,427 | B2 | 1/2012 | Eck et al. |
| 8,105,239 | B2 | 1/2012 | Specht |
| 8,172,754 | B2 | 5/2012 | Watanabe et al. |
| 8,175,368 | B2 | 5/2012 | Sathyanarayana |
| 8,200,313 | B1 | 6/2012 | Rambod et al. |
| 8,211,023 | B2 | 7/2012 | Swan et al. |
| 8,228,347 | B2 | 7/2012 | Beasley et al. |
| 8,298,147 | B2 | 10/2012 | Huennekens et al. |
| 8,303,505 | B2 | 11/2012 | Webler et al. |
| 8,323,202 | B2 | 12/2012 | Roschak et al. |
| 8,328,727 | B2 | 12/2012 | Miele et al. |
| 8,388,541 | B2 | 3/2013 | Messerly et al. |
| 8,409,103 | B2 | 4/2013 | Grunwald et al. |
| 8,449,465 | B2 | 5/2013 | Nair et al. |
| 8,553,954 | B2 | 10/2013 | Saikia |
| 8,556,815 | B2 | 10/2013 | Pelissier et al. |
| 8,585,600 | B2 | 11/2013 | Liu et al. |
| 8,622,913 | B2 | 1/2014 | Dentinger et al. |
| 8,706,457 | B2 | 4/2014 | Hart et al. |
| 8,727,988 | B2 | 5/2014 | Flaherty et al. |
| 8,734,357 | B2 | 5/2014 | Taylor |
| 8,744,211 | B2 | 6/2014 | Owen |
| 8,754,865 | B2 | 6/2014 | Merritt et al. |
| 8,764,663 | B2 | 7/2014 | Smok et al. |
| 8,781,194 | B2 | 7/2014 | Malek et al. |
| 8,781,555 | B2 | 7/2014 | Burnside et al. |
| 8,790,263 | B2 | 7/2014 | Randall et al. |
| 8,849,382 | B2 | 9/2014 | Cox et al. |
| 8,939,908 | B2 | 1/2015 | Suzuki et al. |
| 8,961,420 | B2 | 2/2015 | Zhang |
| 9,022,940 | B2 | 5/2015 | Meier |
| 9,138,290 | B2 | 9/2015 | Hadjicostis |
| 9,155,517 | B2 | 10/2015 | Dunbar et al. |
| 9,204,858 | B2 | 12/2015 | Pelissier et al. |
| 9,220,477 | B2 | 12/2015 | Urabe et al. |
| 9,257,220 | B2 | 2/2016 | Nicholls et al. |
| 9,295,447 | B2 | 3/2016 | Shah |
| 9,320,493 | B2 | 4/2016 | Visveshwara |
| 9,357,980 | B2 | 6/2016 | Toji et al. |
| 9,364,171 | B2 | 6/2016 | Harris et al. |
| 9,427,207 | B2 | 8/2016 | Sheldon et al. |
| 9,445,780 | B2 | 9/2016 | Hossack et al. |
| 9,456,766 | B2 | 10/2016 | Cox et al. |
| 9,456,804 | B2 | 10/2016 | Tamada |
| 9,459,087 | B2 | 10/2016 | Dunbar et al. |
| 9,468,413 | B2 | 10/2016 | Hall et al. |
| 9,492,097 | B2 | 11/2016 | Wilkes et al. |
| 9,521,961 | B2 | 12/2016 | Silverstein et al. |
| 9,554,716 | B2 | 1/2017 | Burnside et al. |
| 9,582,876 | B2 | 2/2017 | Specht |
| 9,597,008 | B2 | 3/2017 | Henkel et al. |
| 9,610,061 | B2 | 4/2017 | Ebbini et al. |
| 9,636,031 | B2 | 5/2017 | Cox |
| 9,649,037 | B2 | 5/2017 | Lowe et al. |
| 9,649,048 | B2 | 5/2017 | Cox et al. |
| 9,702,969 | B2 | 7/2017 | Hope Simpson et al. |
| 9,715,757 | B2 | 7/2017 | Ng et al. |
| 9,717,415 | B2 | 8/2017 | Cohen et al. |
| 9,731,066 | B2 | 8/2017 | Liu et al. |
| 9,814,433 | B2 | 11/2017 | Benishti et al. |
| 9,814,531 | B2 | 11/2017 | Yagi et al. |
| 9,861,337 | B2 | 1/2018 | Patwardhan et al. |
| 9,895,138 | B2 | 2/2018 | Sasaki |
| 9,913,605 | B2 | 3/2018 | Harris et al. |
| 9,949,720 | B2 | 4/2018 | Southard et al. |
| 10,043,272 | B2 | 8/2018 | Forzoni et al. |
| 10,380,919 | B2 | 8/2019 | Savitsky et al. |
| 10,380,920 | B2 | 8/2019 | Savitsky et al. |
| 10,424,225 | B2 | 9/2019 | Nataneli et al. |
| 10,434,278 | B2 | 10/2019 | Dunbar et al. |
| 10,449,330 | B2 | 10/2019 | Newman et al. |
| 10,524,691 | B2 | 1/2020 | Newman et al. |
| 10,674,935 | B2 | 6/2020 | Henkel et al. |

(56) References Cited

U.S. PATENT DOCUMENTS

| | | |
|---|---|---|
| 10,751,509 B2 | 8/2020 | Misener |
| 10,758,155 B2 | 9/2020 | Henkel et al. |
| 10,765,343 B2 | 9/2020 | Henkel et al. |
| 10,896,628 B2 | 1/2021 | Savitsky et al. |
| 11,062,624 B2 | 7/2021 | Savitsky et al. |
| 11,120,709 B2 | 9/2021 | Savitsky et al. |
| 11,311,269 B2 | 4/2022 | Dunbar et al. |
| 11,315,439 B2 | 4/2022 | Savitsky et al. |
| 11,600,201 B1 | 3/2023 | Savitsky et al. |
| 2002/0038088 A1 | 3/2002 | Imran et al. |
| 2002/0148277 A1 | 10/2002 | Umeda |
| 2003/0047126 A1 | 3/2003 | Tomaschko |
| 2003/0060714 A1 | 3/2003 | Henderson et al. |
| 2003/0073900 A1 | 4/2003 | Senarith et al. |
| 2003/0093001 A1 | 5/2003 | Martikainen |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0020926 A1 | 1/2010 | Boese et al. |
| 2010/0106015 A1* | 4/2010 | Norris ............... A61B 17/3403 |
| | | 600/437 |
| 2010/0179428 A1 | 7/2010 | Pedersen et al. |
| 2010/0211026 A2 | 8/2010 | Sheetz et al. |
| 2010/0277305 A1 | 11/2010 | Garner et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0295108 A1 | 12/2011 | Cox et al. |
| 2011/0313293 A1 | 12/2011 | Lindekugel et al. |
| 2012/0179038 A1 | 7/2012 | Meurer et al. |
| 2012/0197132 A1 | 8/2012 | O'Connor |
| 2012/0209121 A1 | 8/2012 | Boudier |
| 2012/0220865 A1 | 8/2012 | Brown et al. |
| 2012/0238875 A1 | 9/2012 | Savitsky et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1* | 8/2013 | Boctor ............... A61B 8/4416 |
| | | 600/476 |
| 2013/0324840 A1 | 12/2013 | Zhongping et al. |
| 2014/0005530 A1 | 1/2014 | Liu et al. |
| 2014/0031690 A1 | 1/2014 | Toji et al. |
| 2014/0036091 A1 | 2/2014 | Zalev et al. |
| 2014/0073976 A1 | 3/2014 | Fonte et al. |
| 2014/0100440 A1 | 4/2014 | Cheline et al. |
| 2014/0155737 A1 | 6/2014 | Manzke et al. |
| 2014/0180098 A1 | 6/2014 | Flaherty et al. |
| 2014/0188133 A1 | 7/2014 | Misener |
| 2014/0188440 A1 | 7/2014 | Donhowe et al. |
| 2014/0257104 A1 | 9/2014 | Dunbar et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0209113 A1 | 7/2015 | Burkholz et al. |
| 2015/0209526 A1 | 7/2015 | Matsubara et al. |
| 2015/0294497 A1 | 10/2015 | Ng et al. |
| 2015/0297097 A1 | 10/2015 | Matsubara et al. |
| 2015/0327841 A1 | 11/2015 | Banjanin et al. |
| 2015/0359991 A1 | 12/2015 | Dunbar et al. |
| 2016/0029995 A1 | 2/2016 | Navratil et al. |
| 2016/0029998 A1 | 2/2016 | Brister et al. |
| 2016/0058420 A1 | 3/2016 | Cinthio et al. |
| 2016/0100970 A1 | 4/2016 | Brister et al. |
| 2016/0101263 A1 | 4/2016 | Blumenkranz et al. |
| 2016/0113699 A1 | 4/2016 | Sverdlik et al. |
| 2016/0120607 A1 | 5/2016 | Sorotzkin et al. |
| 2016/0143622 A1 | 5/2016 | Xie et al. |
| 2016/0166232 A1 | 6/2016 | Merritt |
| 2016/0202053 A1 | 7/2016 | Walker et al. |
| 2016/0213398 A1* | 7/2016 | Liu ............... A61B 8/0891 |
| 2016/0278743 A1 | 9/2016 | Kawashima |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0079548 A1 | 3/2017 | Silverstein et al. |
| 2017/0086785 A1 | 3/2017 | Bjaerum |
| 2017/0100092 A1 | 4/2017 | Kruse et al. |
| 2017/0164923 A1 | 6/2017 | Matsumoto |
| 2017/0172424 A1 | 6/2017 | Eggers et al. |
| 2017/0188839 A1 | 7/2017 | Tashiro |
| 2017/0196535 A1 | 7/2017 | Arai et al. |
| 2017/0215842 A1 | 8/2017 | Ryu et al. |
| 2017/0259013 A1* | 9/2017 | Boyden ............... G16H 30/40 |
| 2017/0265840 A1 | 9/2017 | Bharat et al. |
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0225993 A1 | 8/2018 | Buras et al. |
| 2018/0228465 A1 | 8/2018 | Southard et al. |
| 2018/0235576 A1 | 8/2018 | Brannan |
| 2018/0250078 A1 | 9/2018 | Shochat et al. |
| 2018/0272108 A1 | 9/2018 | Padilla et al. |
| 2018/0279996 A1 | 10/2018 | Cox et al. |
| 2018/0286287 A1 | 10/2018 | Razzaque |
| 2018/0310955 A1 | 11/2018 | Lindekugel et al. |
| 2018/0317881 A1 | 11/2018 | Astigarraga et al. |
| 2018/0366035 A1 | 12/2018 | Dunbar et al. |
| 2019/0060014 A1 | 2/2019 | Hazelton et al. |
| 2019/0069923 A1* | 3/2019 | Wang ............... A61B 17/3403 |
| 2019/0076121 A1 | 3/2019 | Southard et al. |
| 2019/0088019 A1 | 3/2019 | Prevrhal et al. |
| 2019/0105017 A1* | 4/2019 | Hastings ............... A61B 8/4444 |
| 2019/0117190 A1 | 4/2019 | Djajadiningrat et al. |
| 2019/0223757 A1 | 7/2019 | Durfee |
| 2019/0239850 A1 | 8/2019 | Dalvin et al. |
| 2019/0282324 A1 | 9/2019 | Freeman et al. |

(56) References Cited

U.S. PATENT DOCUMENTS

| | | |
|---|---|---|
| 2019/0298457 A1 | 10/2019 | Bharat |
| 2019/0307516 A1 | 10/2019 | Schotzko et al. |
| 2019/0339525 A1 | 11/2019 | Yanof et al. |
| 2019/0355278 A1 | 11/2019 | Sainsbury et al. |
| 2019/0365348 A1 | 12/2019 | Toume et al. |
| 2020/0041261 A1 | 2/2020 | Bernstein et al. |
| 2020/0069285 A1 | 3/2020 | Annangi et al. |
| 2020/0113540 A1 | 4/2020 | Gijsbers et al. |
| 2020/0129136 A1 | 4/2020 | Harding et al. |
| 2020/0188028 A1 | 6/2020 | Feiner et al. |
| 2020/0230391 A1 | 7/2020 | Burkholz et al. |
| 2021/0007710 A1 | 1/2021 | Douglas |
| 2021/0045716 A1 | 2/2021 | Shiran et al. |
| 2021/0166583 A1 | 6/2021 | Buras et al. |
| 2021/0307838 A1 | 10/2021 | Xia et al. |
| 2021/0353255 A1 | 11/2021 | Schneider et al. |
| 2021/0402144 A1 | 12/2021 | Messerly |
| 2022/0022969 A1 | 1/2022 | Misener |
| 2022/0031965 A1 | 2/2022 | Durfee |
| 2022/0039685 A1 | 2/2022 | Misener et al. |
| 2022/0039777 A1 | 2/2022 | Durfee |
| 2022/0096797 A1 | 3/2022 | Prince |
| 2022/0117582 A1 | 4/2022 | McLaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0211442 A1 | 7/2022 | McLaughlin et al. |
| 2022/0381630 A1 | 12/2022 | Sowards et al. |
| 2023/0113291 A1 | 4/2023 | de Wild et al. |
| 2023/0240643 A1 | 8/2023 | Cermak et al. |
| 2023/0389893 A1 | 12/2023 | Misener et al. |
| 2024/0008929 A1 | 1/2024 | Misener et al. |
| 2024/0050061 A1 | 2/2024 | McLaughlin et al. |
| 2024/0058074 A1 | 2/2024 | Misener |
| 2024/0062678 A1 | 2/2024 | Sowards et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 3181083 A1 | 6/2017 |
| EP | 3530221 A1 | 8/2019 |
| JP | 2000271136 A | 10/2000 |
| JP | 2014150928 A | 8/2014 |
| JP | 2018175547 A | 11/2018 |
| KR | 20180070878 A | 6/2018 |
| KR | 20190013133 A * | 2/2019 |
| WO | 2013059714 A1 | 4/2013 |
| WO | 2014/115150 A1 | 7/2014 |
| WO | 2014174305 A2 | 10/2014 |
| WO | 2015/017270 A1 | 2/2015 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2018206473 A1 | 11/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020102665 A1 | 5/2020 |
| WO | 2020/186198 A1 | 9/2020 |
| WO | 2022/031762 A1 | 2/2022 |
| WO | 2022/072727 A2 | 4/2022 |
| WO | 2022/081904 A1 | 4/2022 |
| WO | 2022-203713 A2 | 9/2022 |
| WO | 2022263763 A1 | 12/2022 |
| WO | 2023235435 A1 | 12/2023 |
| WO | 2024010940 A1 | 1/2024 |
| WO | 2024039608 A1 | 2/2024 |
| WO | 2024039719 A1 | 2/2024 |

OTHER PUBLICATIONS

U.S. Appl. No. 17/380,767, filed Jul. 20, 2021 Non-Final Office Action dated Mar. 6, 2023.
U.S. Appl. No. 17/393,283, filed Aug. 3, 2021 Non-Final Office Action dated Mar. 31, 2023.
EZono, eZSimulator, https://www.ezono.com/en/ezsimulator/, last accessed Sep. 13, 2022.
Sonosim, https://sonosim.com/ultrasound-simulation/? last accessed Sep. 13, 2022.
U.S. Appl. No. 17/397,486, filed Aug. 9, 2021 Restriction Requirement dated Aug. 12, 2022.
PCT/US2021/050973 filed Sep. 17, 2021 International Search Report and Written Opinion dated Nov. 7, 2022.
U.S. Appl. No. 17/380,767, filed Jul. 20, 2021 Restriction Requirement dated Dec. 15, 2022.
U.S. Appl. No. 17/393,283, filed Aug. 3, 2021 Restriction Requirement dated Jan. 12, 2023.
U.S. Appl. No. 17/397,486, filed Aug. 9, 2021 Non-Final Office Action dated Jan. 23, 2023.
U.S. Appl. No. 17/501,909, filed Oct. 14, 2021 Restriction Requirement dated Feb. 1, 2023.
Khsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XP036387340, ISSN: 1346-4523, DOI: 10.1007/S10396-017-0789-2 [retrieved on Apr. 19, 2017].
Pagoulatos, N. et al. "New spatial localizer based on fiber optics with applications in 3D ultrasound imaging" Proceeding of Spie, vol. 3976 (Apr. 18, 2000; Apr. 18, 2000).
PCT/US2021/042369 filed Jul. 20, 2021 International Search Report and Written Opinion dated Oct. 25, 2021.
PCT/US2021/044419 filed Aug. 3, 2021 International Search Report and Written Opinion dated Nov. 19, 2021.
PCT/US2021/055076 filed Oct. 14, 2021 International Search Report and Written Opinion dated Mar. 25, 2022.
PCT/US12/61182 International Seach Report and Written Opinion dated Mar. 11, 2013.
PCT/US2021/049294 filed Sep. 7, 2021 International Search Report and Written Opinion dated Dec. 8, 2021.
PCT/US2021/049712 filed Sep. 9, 2021 International Search Report and Written Opinion dated Dec. 14, 2021.
PCT/US2021/052055 filed Sep. 24, 2021 International Search Report and Written Opinion dated Dec. 20, 2021.
U.S. Appl. No. 13/656,563, filed Oct. 19, 2012 Decision on Appeal dated Nov. 1, 2017.
U.S. Appl. No. 13/656,563, filed Oct. 19, 2012 Examiner's Answer dated Nov. 16, 2015.
U.S. Appl. No. 13/656,563, filed Oct. 19, 2012 Final Office Action dated Dec. 5, 2014.
U.S. Appl. No. 13/656,563, filed Oct. 19, 2012 Non-Final Office Action dated Jul. 18, 2014.
U.S. Appl. No. 15/650,474, filed Jul. 14, 2017 Final Office Action dated Jun. 2, 2020.
U.S. Appl. No. 15/650,474, filed Jul. 14, 2017 Non-Final Office Action dated Dec. 16, 2019.
U.S. Appl. No. 15/650,474, filed Jul. 14, 2017 Notice of Allowance dated Dec. 1, 2020.
U.S. Appl. No. 15/650,474, filed Jul. 14, 2017 Notice of Allowance dated Mar. 1, 2021.
U.S. Appl. No. 15/951,903, filed Apr. 12, 2018 Advisory Action dated Dec. 22, 2020.
U.S. Appl. No. 15/951,903, filed Apr. 12, 2018 Examiner's Answer dated Jun. 3, 2021.
U.S. Appl. No. 15/951,903, filed Apr. 12, 2018 Final Office Action dated Oct. 13, 2020.
U.S. Appl. No. 15/951,903, filed Apr. 12, 2018 Non-Final Office Action dated May 22, 2020.
U.S. Appl. No. 17/020,476, filed Sep. 14, 2020 Non-Final Office Action dated Feb. 9, 2022.
Lu Zhenyu et al "Recent advances in 5 robot-assisted echography combining perception control and cognition." Cognitive Computa-

(56) References Cited

OTHER PUBLICATIONS tion and Systems the Institution of Engineering and Technology, Michael Faraday House, Six Hills Way, Stevenage Herts. SG1 2AY UK vol. 2 No. 3 Sep. 2, 2020 (Sep. 2, 2020).
PCT/US2021/045218 filed Aug. 9, 2021 International Search Report and Written Opinion dated Nov. 23, 2021.
PCT/US2021/049123 filed Sep. 3, 2021 International Search Report and Written Opinion dated Feb. 4, 2022.
PCT/US2021/053018 filed Sep. 30, 2021 International Search Report and Written Opinion dated May 3, 2022.
PCT/US2021/060622 filed Nov. 23, 2021 International Search Report and Written Opinion dated Mar. 3, 2022.
PCT/US2021/061267 filed Nov. 30, 2021 International Search Report and Written Opinion dated Mar. 9, 2022.
PCT/US2021/061276 filed Nov. 30, 2021 International Search Report and Written Opinion dated Mar. 9, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.
U.S. Appl. No. 15/951,903, filed Apr. 12, 2018 Board Decision dated Apr. 20, 2022.
U.S. Appl. No. 15/951,903, filed Apr. 12, 2018 Notice of Allowance dated May 2, 2022.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).
U.S. Appl. No. 17/397,486, filed Aug. 9, 2021 Final Office Action dated Aug. 4, 2023.
U.S. Appl. No. 17/501,909, filed Oct. 14, 2021 Non-Final Office Action dated Jun. 6, 2023.
U.S. Appl. No. 17/832,389, filed Jun. 3, 2022 Restriction Requirement dated Jul. 13, 2023.
PCT/US2023/024067 filed May 31, 2023 International Search Report and Written Opinion dated Sep. 15, 2023.
PCT/US2023/027147 filed Jul. 7, 2023 International Search Report and Written Opinion dated Oct. 2, 2023.
PCT/US2023/030160 filed Aug. 14, 2023 International Search Report and Written Opinion dated Oct. 23, 2023.
Practical guide for safe central venous catheterization and management 2017 Journal of Anesthesia vol. 34 published online Nov. 30, 2019 pp. 167-186.
U.S. Appl. No. 17/380,767, filed Jul. 20, 2021 Notice of Allowance dated Aug. 31, 2023.
U.S. Appl. No. 17/393,283, filed Aug. 3, 2021 Final Office Action dated Oct. 16, 2023.
U.S. Appl. No. 17/397,486, filed Aug. 9, 2021 Advisory Action dated Oct. 5, 2023.
U.S. Appl. No. 17/832,389, filed Jun. 3, 2022 Non-Final Office Action dated Oct. 6, 2023.
U.S. Appl. No. 17/861,031, filed Jul. 8, 2022 Non-Final Office Action dated Sep. 14, 2023.
U.S. Appl. No. 17/393,283, filed Aug. 3, 2021 Advisory Action dated Jan. 19, 2024.
U.S. Appl. No. 17/478,754, filed Sep. 17, 2021 Restriction Requirement dated Jan. 22, 2024.
U.S. Appl. No. 17/501,909, filed Oct. 14, 2021 Advisory Action dated Jan. 24, 2024.
U.S. Appl. No. 17/501,909, filed Oct. 14, 2021 Final Office Action dated Nov. 21, 2023.
U.S. Appl. No. 17/832,389, filed Jun. 3, 2022 Final Office Action dated Jan. 25, 2024.
PCT/US2023/030347 filed Aug. 16, 2023 International Search Report and Written Opinion dated Nov. 6, 2023.
U.S. Appl. No. 17/393,283, filed Aug. 3, 2021 Non-Final Office Action dated Feb. 29, 2024.
U.S. Appl. No. 17/397,486, filed Aug. 9, 2021 Non-Final Office Action dated Mar. 1, 2024.
U.S. Appl. No. 17/501,909, filed Oct. 14, 2021 Non-Final Office Action dated Mar. 21, 2024.
U.S. Appl. No. 17/832,389, filed Jun. 3, 2022 Advisory Action dated Apr. 5, 2024.
U.S. Appl. No. 17/832,389, filed Jun. 3, 2022 Notice of Allowance dated May 15, 2024.
U.S. Appl. No. 17/861,031, filed Jul. 8, 2022 Final Office Action dated Mar. 15, 2024.
U.S. Appl. No. 17/397,486, filed Aug. 9, 2021 Notice of Allowance dated Jul. 10, 2024.
U.S. Appl. No. 17/478,754, filed Sep. 17, 2021 Non-Final Office Action dated Jul. 1, 2024.
U.S. Appl. No. 17/501,909, filed Oct. 14, 2021 Final Office Action dated Aug. 5, 2024.
U.S. Appl. No. 17/861,031, filed Jul. 8, 2022 Advisory Action dated Jun. 7, 2024.
U.S. Appl. No. 17/861,031, filed Jul. 8, 2022 Notice of Allowance dated Jul. 3, 2024.
U.S. Appl. No. 18/385,101, filed Oct. 30, 2023 Notice of Allowance dated Aug. 20, 2024.

* cited by examiner

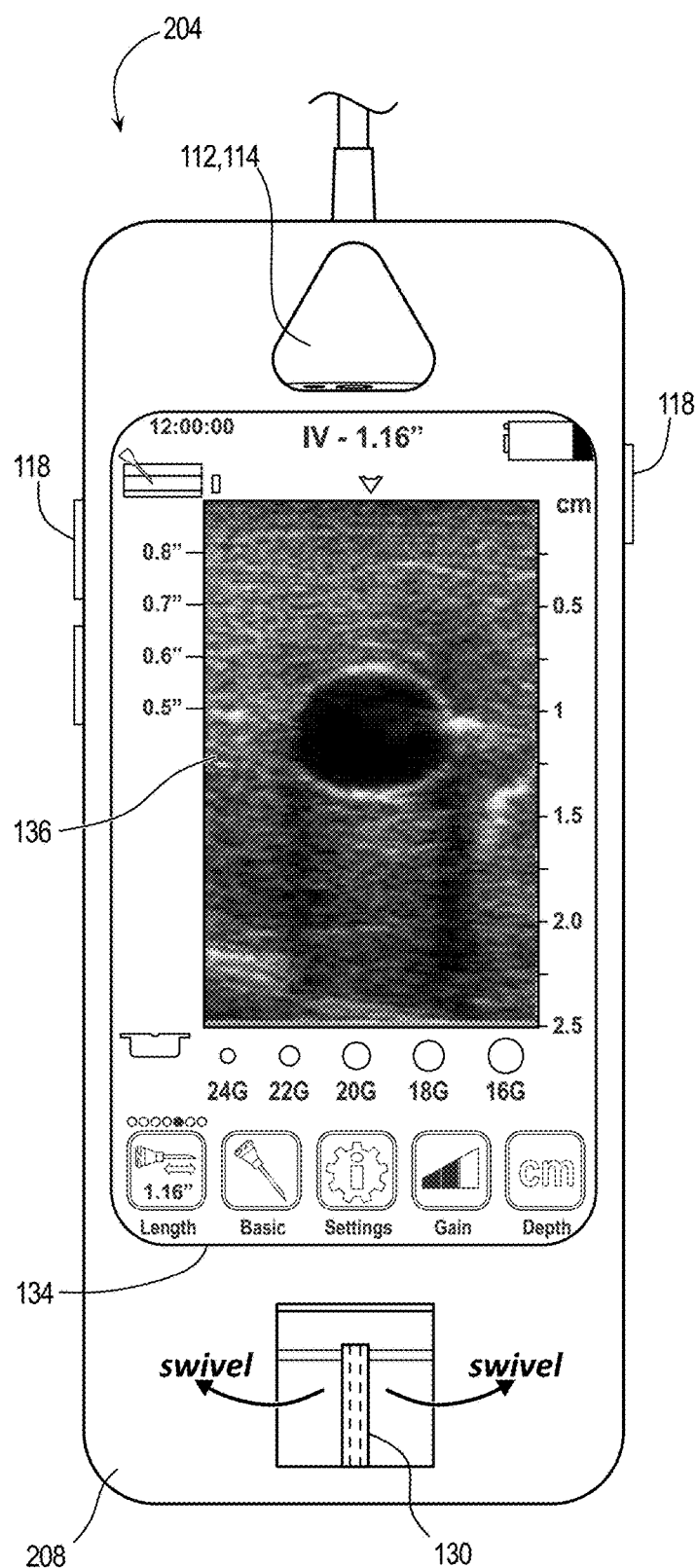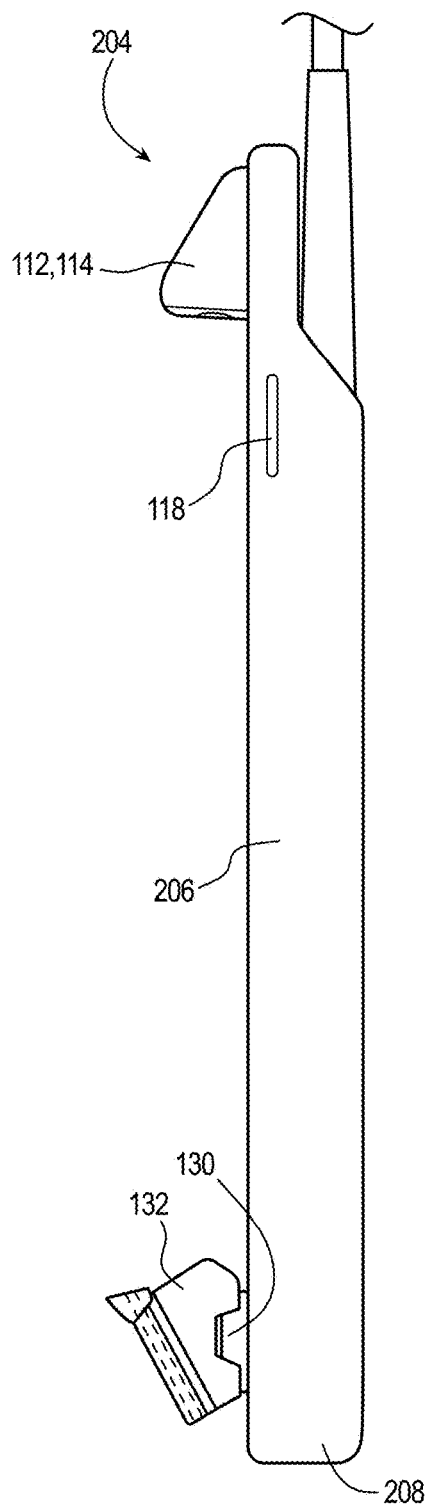
FIG. 4
FIG. 5

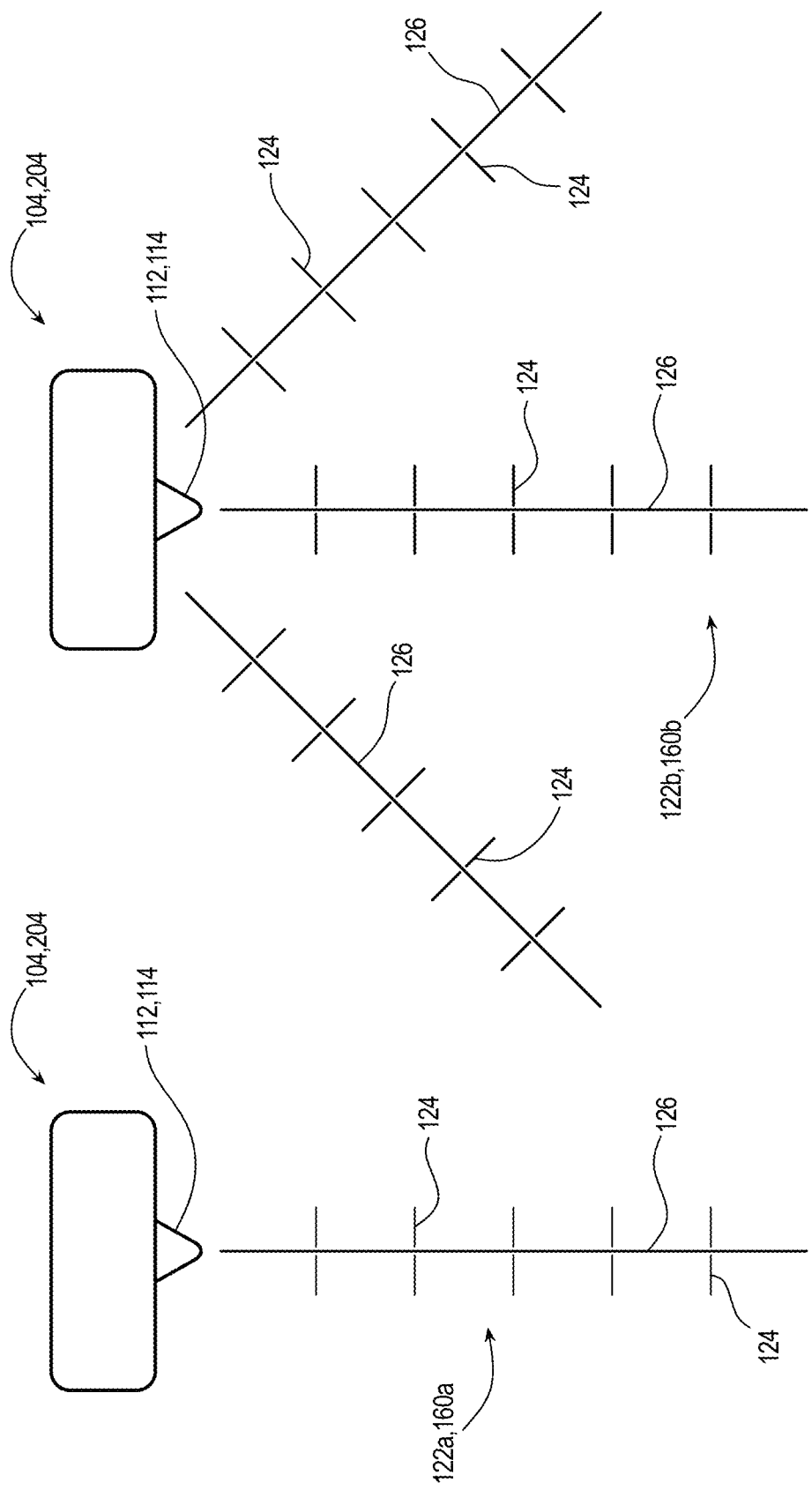

ULTRASOUND SYSTEMS AND METHODS FOR SUSTAINED SPATIAL ATTENTION

PRIORITY

This application claims the benefit of priority to U.S. Provisional Patent Application No. 63/086,971, filed Oct. 2, 2020, which is incorporated by reference in its entirety into this application.

BACKGROUND

A variety of ultrasound systems exist including wired or wireless ultrasound probes for ultrasound imaging. Whether wired or wireless, an ultrasound system such as the foregoing requires a clinician to switch his or her spatial attention between different spatial regions, particularly between 1) a relatively close ultrasound probe being used for ultrasound imaging and 2) a relatively distant display rendering corresponding ultrasound images. Having to switch spatial attention between the ultrasound probe and the display can be difficult when ultrasound imaging and attempting to simultaneously establish an insertion site with a needle, place a vascular access device ("VAD") such as a catheter in a blood vessel of a patient at the insertion site, or the like. Such difficulties can be pronounced for less experienced clinicians, older clinicians having reduced lens flexibility in their eyes, etc. Ultrasound systems are needed that do not require clinicians to continuously switch their spatial attention between different spatial regions.

Disclosed herein are ultrasound systems and methods for sustained spatial attention in one or more spatial regions.

SUMMARY

Disclosed herein is an ultrasound probe including, in some embodiments, a probe body, a probe head extending from a distal end of the probe body, and a camera integrated into a side of the ultrasound probe. The probe head includes a plurality of ultrasonic transducers arranged in an array. The camera is configured for recording one or more still or moving images of a procedural field with a depth of field including a plane of a distal end of the probe head and a field of view including a spatial region about the probe head.

In some embodiments, the ultrasound probe further includes a light-pattern projector integrated into the side of the ultrasound probe including the camera. The light-pattern projector is configured to project a light pattern in the spatial region about the probe head focused in the plane of the distal end of the probe head. The light pattern is configured for guided insertion of a needle into an anatomical target under the probe head in the procedural field.

In some embodiments, the light pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the light pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the ultrasound probe further includes a needle-guide holder extending from a side of the probe head in common with the side of the ultrasound probe including the camera.

In some embodiments, the ultrasound probe further includes a single-use needle guide coupled to the needle-guide holder. The needle-guide holder, the needle guide, or a combination of the needle-guide holder and the needle guide includes at least one degree of freedom enabling the needle guide to swivel between sides of the ultrasound probe.

Also disclosed herein is an ultrasound system including, in some embodiments, a console and an ultrasound probe. The console includes a display configured to render on a display screen thereof ultrasound images and one or more still or moving images of a procedural field. The ultrasound probe includes a probe body, a probe head extending from a distal end of the probe body, and a camera integrated into a side of the ultrasound probe. The probe head includes a plurality of ultrasonic transducers arranged in an array. The camera is configured for recording the one-or-more still or moving images of the procedural field with a depth of field including a plane of a distal end of the probe head and a field of view including a spatial region about the probe head.

In some embodiments, the ultrasound probe further includes a needle-guide holder extending from a side of the probe head in common with the side of the ultrasound probe including the camera.

In some embodiments, the ultrasound probe further includes a single-use needle guide coupled to the needle-guide holder. The needle-guide holder, the needle guide, or a combination of the needle-guide holder and the needle guide includes at least one degree of freedom enabling the needle guide to swivel between sides of the ultrasound probe.

In some embodiments, the ultrasound probe further includes a light-pattern projector integrated into the side of the ultrasound probe including the camera. The light-pattern projector is configured to project a light pattern in the spatial region about the probe head focused in the plane of the distal end of the probe head. The light pattern is configured for guided insertion of a needle into an anatomical target under the probe head in the procedural field.

In some embodiments, the light pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the light pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the one-or-more still or moving images show both the light pattern in the spatial region about the probe head and the needle in relation to the light pattern when both the light pattern and the needle are present in the spatial region about the probe head. The one-or-more still or moving images show both the light pattern and the needle in relation to the light pattern for the guided insertion of the needle into the anatomical target under the probe head optionally on the display.

In some embodiments, the display is further configured to render on the display screen one or more overlying needle trajectories lying over the ultrasound images in accordance with one or more depths accessible by the needle indicated by the light pattern. The one-or-more overlying needle trajectories are configured for the guided insertion of the needle into the anatomical target under the probe head on the display.

In some embodiments, the display is further configured to render on the display screen an overlying pattern lying over the one-or-more still or moving images. The overlying pattern is configured for guided insertion of a needle into an anatomical target under the probe head on the display.

In some embodiments, the overlying pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the overlying pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the one-or-more still or moving images show the needle in relation to the overlying pattern when the needle is present in the spatial region about the probe head. The one-or-more still or moving images show the needle in relation to the overlying pattern for the guided insertion of the needle into the anatomical target under the probe head optionally on the display.

In some embodiments, the display is further configured to render on the display screen one or more overlying needle trajectories lying over the ultrasound images in accordance with one or more depths accessible by the needle indicated by the overlying pattern. The one-or-more overlying needle trajectories are configured for the guided insertion of the needle into an anatomical target under the probe head on the display.

Also disclosed herein is an ultrasound probe including, in some embodiments, a probe body, a probe head extending from a distal end of the probe body, and a display integrated into a side of the ultrasound probe. The probe head includes a plurality of ultrasonic transducers arranged in an array. The display is configured to render on a display screen thereof ultrasound images and one or more overlying needle trajectories lying over the ultrasound images. The one-or-more overlying needle trajectories are configured for guided insertion of a needle into an anatomical target under the probe head on the display.

In some embodiments, the ultrasound probe further includes a light-pattern projector integrated into the side of the ultrasound probe including the display. The light-pattern projector is configured to project a light pattern in a spatial region about the probe head focused in a plane of a distal end of the probe head. The light pattern is configured for the guided insertion of the needle into the anatomical target under the probe head in the procedural field.

In some embodiments, the light pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the light pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the one-or-more overlying needle trajectories lying over the ultrasound images are in accordance with one or more depths accessible by the needle indicated by the light pattern.

In some embodiments, the ultrasound probe further includes a needle-guide holder extending from the side of the ultrasound probe including the display.

In some embodiments, the ultrasound probe further includes a single-use needle guide coupled to the needle-guide holder. The needle-guide holder, the needle guide, or a combination of the needle-guide holder and the needle guide includes at least one degree of freedom enabling the needle guide to swivel between sides of the ultrasound probe.

Also disclosed herein is a method of an ultrasound system including, in some embodiments, an ultrasound probe-obtaining step, an ultrasound probe-moving step, a recording step, an ultrasound image-monitoring step, and a needle-inserting step. The ultrasound probe-obtaining step includes obtaining an ultrasound probe. The ultrasound probe includes a probe body, a probe head extending from a distal end of the probe body, and a camera integrated into a side of the ultrasound probe. The ultrasound probe-moving step includes moving the ultrasound probe over a patient while the ultrasound probe emits generated ultrasound signals into the patient from ultrasonic transducers in the probe head and receives reflected ultrasound signals from the patient by the ultrasonic transducers. The recording step includes recording one or more still or moving images of a procedural field with a depth of field including a plane of a distal end of the probe head and a field of view including a spatial region about the probe head. The ultrasound image-monitoring step includes monitoring ultrasound images rendered on a display screen of a display associated with a console of the ultrasound system to identify an anatomical target of the patient under the probe head. The needle-inserting step includes inserting a needle into the anatomical target. Optionally, the inserting of the needle is guided by the display with reference to the one-or-more still or moving images rendered on the display screen thereof.

In some embodiments, the method further includes a needle guide-attaching step. The needle guide-attaching step includes attaching a needle guide to a needle-guide holder extending from the probe body. The needle guide includes a needle through hole configured to direct the needle into the patient under the probe head at a needle-insertion angle with respect to the plane of the probe head.

In some embodiments, the method further includes a needle guide-swiveling step. The needle guide-swiveling step includes swiveling the needle guide between sides of the ultrasound probe to find a suitable needle trajectory before the needle-inserting step. The needle-guide holder, the needle guide, or a combination of the needle-guide holder and the needle guide includes at least one degree of freedom enabling the swiveling of the needle guide.

In some embodiments, the needle is guided in the procedural field during the needle-inserting step in accordance with a light pattern in the spatial region about the probe head. The light pattern is projected from a light-pattern projector integrated into the side of the ultrasound probe including the camera and focused in the plane of the distal end of the probe head for guiding the needle in the procedural field.

In some embodiments, the light pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the light pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the needle is further guided on the display during the needle-inserting step. The one-or-more still or moving images show both the light pattern in the spatial region about the probe head and the needle in relation to the light pattern for guiding the needle on the display.

In some embodiments, the needle is further guided on the display during the needle-inserting step. The ultrasound images show one or more overlying needle trajectories in accordance with one or more depths accessible by the needle indicated by the light pattern for guiding the needle on the display.

In some embodiments, the needle is guided on the display during the needle-inserting step in accordance with an overlying pattern rendered over the one-or-more still or moving images on the display screen for guiding the needle on the display.

In some embodiments, the overlying pattern includes periodic hash marks along one or more rays radiating from a central axis of the ultrasound probe in the plane of the probe head. Each hash mark of the hash marks corresponds to a depth under the probe head accessible by the needle along an associated ray at a needle-insertion angle with respect to the plane of the probe head.

In some embodiments, the overlying pattern includes periodic concentric circular arcs bound between two or more rays radiating from a central axis of the ultrasound probe in the plane of the probe head. Each circular arc of the circular arcs corresponds to a depth under the probe head accessible by the needle along an associated ray at a needle-insertion angle with respect to the plane of the probe head.

In some embodiments, the needle is further guided on the display during the needle-inserting step. The ultrasound images show one or more overlying needle trajectories in accordance with one or more depths accessible by the needle indicated by the overlying pattern for guiding the needle on the display.

These and other features of the concepts provided herein will become more apparent to those of skill in the art in view of the accompanying drawings and following description, which describe particular embodiments of such concepts in greater detail.

DRAWINGS

FIG. 4 illustrates a front view of the ultrasound probe of FIG. 3 in accordance with some embodiments.

FIG. 5 illustrates a side view of the ultrasound probe of FIG. 3 in accordance with some embodiments.

FIG. 7 illustrates a schematic of a first light pattern or first overlying pattern in accordance with some embodiments.

FIG. 8 illustrates a schematic of a second light pattern or a second overlying pattern in accordance with some embodiments.

DESCRIPTION

Figure 1:
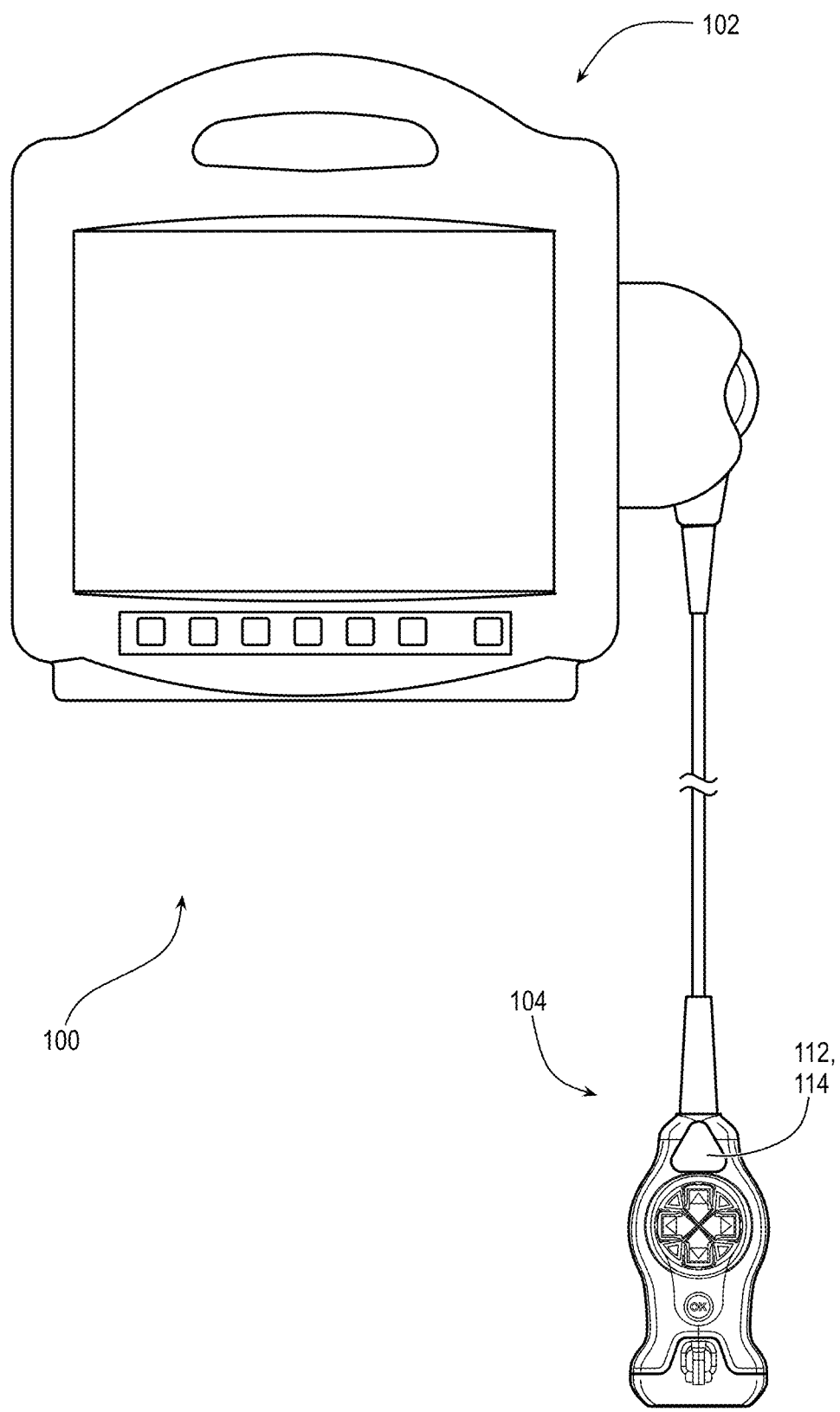
FIG. 1 illustrates an ultrasound system with a first ultrasound probe in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or "proximal section" of, for example, a catheter includes a portion or section of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal section, or the proximal length of the catheter can include the proximal end of the catheter; however, the proximal portion, the proximal section, or the proximal length of the catheter need not include the proximal end of the catheter. That is, unless context suggests otherwise, the proximal portion, the proximal section, or the proximal length of the catheter is not a terminal portion or terminal length of the catheter.

With respect to "distal," a "distal portion" or a "distal section" of, for example, a catheter includes a portion or section of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal section, or the distal length of the catheter can include the distal end of the catheter; however, the distal portion, the distal section, or the distal length of the catheter need not include the distal end of the catheter. That is, unless context suggests otherwise, the distal portion, the distal section, or the distal length of the catheter is not a terminal portion or terminal length of the catheter.

Unless defined otherwise, all technical and scientific terms used herein have the same meaning as commonly understood by those of ordinary skill in the art.

As set forth above, a variety of ultrasound systems exist including wired or wireless ultrasound probes for ultrasound imaging. Whether wired or wireless, an ultrasound system such as the foregoing requires a clinician to switch his or her spatial attention between different spatial regions, particularly between 1) a relatively close ultrasound probe being used for ultrasound imaging and 2) a relatively distant display rendering corresponding ultrasound images. Having to switch spatial attention between the ultrasound probe and the display can be difficult when ultrasound imaging and attempting to simultaneously establish an insertion site with a needle, place a VAD such as a catheter in a blood vessel of a patient at the insertion site, or the like. Such difficulties can be pronounced for less experienced clinicians, older clinicians having reduced lens flexibility in their eyes, etc. Ultrasound systems are needed that do not require clinicians to continuously switch their spatial attention between different spatial regions.

Disclosed herein are ultrasound systems and methods for sustained spatial attention. For example, an ultrasound system can include a console and an ultrasound probe. A display of the console can be configured to display ultrasound images and one or more still or moving images of a procedural field. The ultrasound probe can include a camera integrated into the ultrasound probe for recording the one-or-more still or moving images of the procedural field with a depth of field including a distal end of a probe head and a field of view including a spatial region about the probe head. With the one-or-more still or moving images displayed along with the ultrasound images, a clinician need not switch his or her spatial attention between spatial regions such as the procedural field and the display quite as frequently as with existing ultrasound systems, thereby sustaining spatial attention in one or more spatial regions. These and other features will become more apparent to those of skill in the art in view of the accompanying drawings and following description, which describe particular embodiments in greater detail.

Ultrasound Systems

Figure 3:
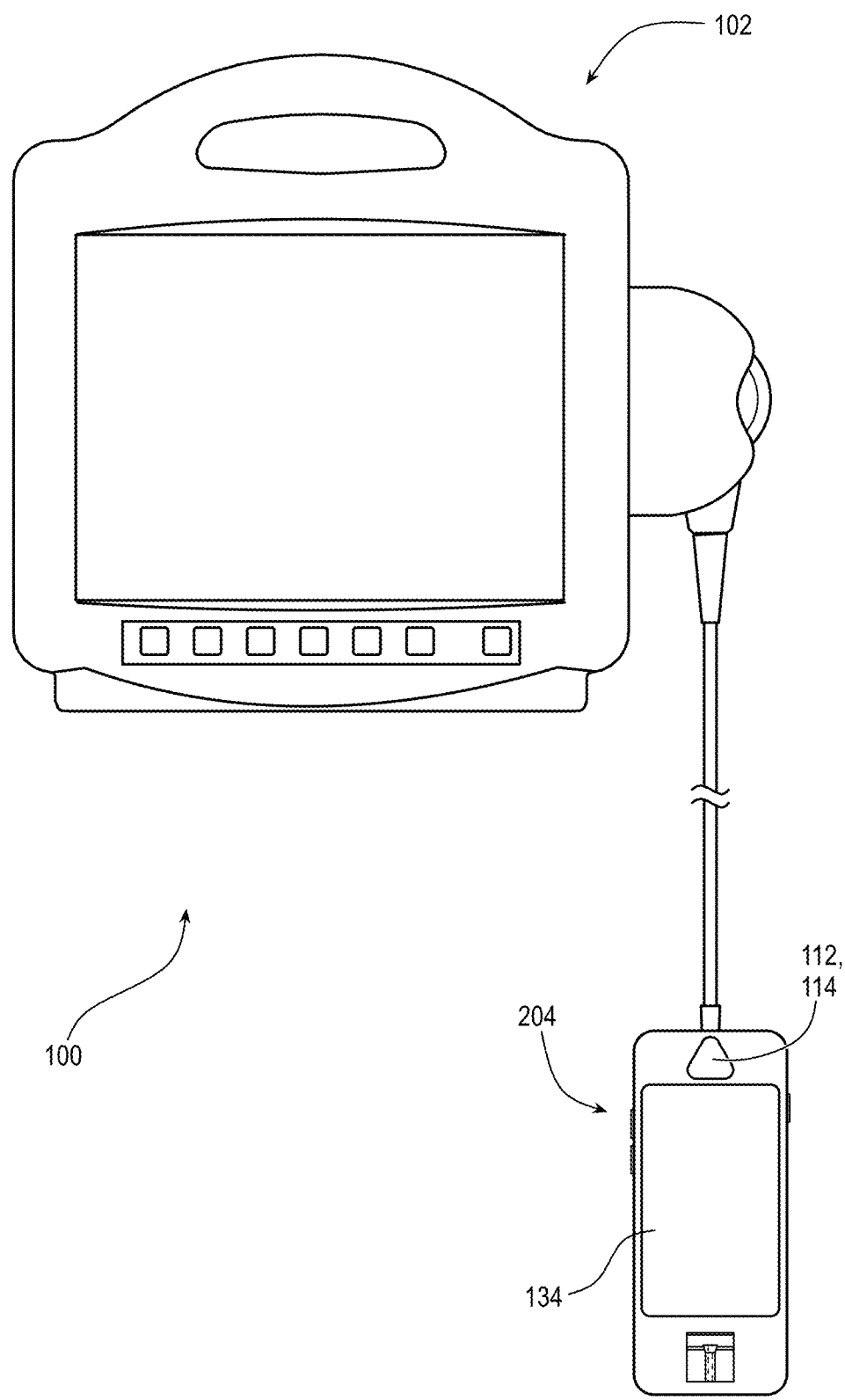
FIG. 3 illustrates the ultrasound system with a second ultrasound probe in accordance with some embodiments.

FIGS. 1 and 3 illustrate an ultrasound system 100 including a console 102 and either a first ultrasound probe 104 or a second ultrasound probe 204 in accordance with some embodiments.

Figure 2:
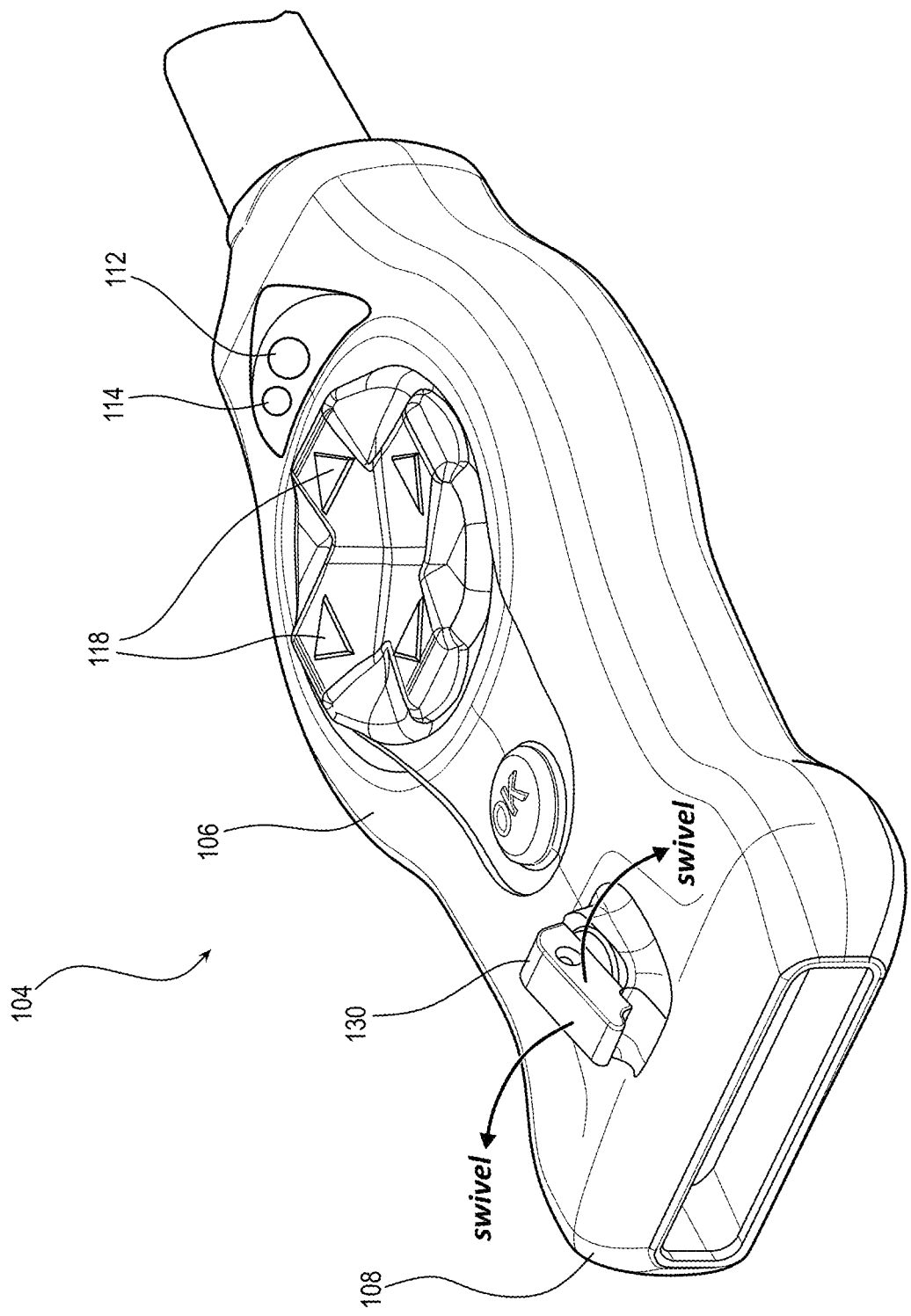
FIG. 2 illustrates a perspective view of the ultrasound probe of FIG. 1 in accordance with some embodiments.

FIG. 2 illustrates a perspective view of the ultrasound probe 104 in accordance with some embodiments.

As shown, the ultrasound probe 104 includes a probe body 106, a probe head 108 extending from a distal end of the probe body 106, and a plurality of ultrasonic transducers 110 arranged in an array in the probe head 108.

The ultrasound probe 104 can also include a camera 112 integrated into a side of the ultrasound probe 104, a light-pattern projector 114 (e.g., a laser light-pattern projector) integrated into the side of the ultrasound probe 104, or both the camera 112 and the light-pattern projector 114 integrated into the side of the ultrasound probe 104. Notably, the side of the ultrasound probe 104 including the camera 112 or the light-pattern projector 114 is shown in FIG. 2 as a major side of the ultrasound probe 104, specifically a top side (or front face) of the ultrasound probe 104, which is convenient for an out-of-plane view of a needle 116 (see FIG. 6) when establishing an insertion site with the needle 116 as set forth in the method below. In addition, the foregoing side of the ultrasound probe 104 conveniently includes various buttons 118 of the ultrasound probe 104 useful for operating the ultrasound probe 104 or 204 or the ultrasound system 100 while establishing an insertion site with the needle 116. That said, the side of the ultrasound probe 104 including the camera 112 or the light-pattern projector 114 can alternatively be a minor side of the ultrasound probe 104, which is convenient for an in-plane view of the needle 116 when establishing an insertion site with the needle 116 as set forth in the method below.

The camera 112 is configured for recording one or more still or moving images 120 (see FIGS. 10 and 11) of a procedural field including a subject portion of a patient therein with a depth of field including a plane of a distal end of the probe head 108 and a field of view including a spatial region about the probe head 108. As set forth in more detail below, the one-or-more still or moving images 120 can be rendered on the display screen of the display 158 along with the ultrasound images 136 associated therewith, which allows a clinician to sustain spatial attention on the display 158 when establishing an insertion site with the needle 116, thereby obviating the clinician from frequently switching his or her spatial attention between the display 158 and the procedural field as done with existing ultrasound systems.

The light-pattern projector 114 is configured to project a light pattern 122 in the spatial region about the probe head 108 focused in the plane of the distal end of the probe head 108, thereby including the foregoing subject portion of the patient in the procedural field. The light pattern 122 is configured for guided insertion of the needle 116 into an anatomical target under the probe head 108 in the procedural field. Similar to the one-or-more still or moving images 120 when rendered on the display screen of the display 158, the light pattern 122 when projected in the spatial region about the probe head 108 allows a clinician to sustain spatial attention in the procedural field when establishing an insertion site with the needle 116 as set forth in the method below, thereby obviating the clinician from frequently switching his or her spatial attention between the procedural field and the display 158 as done with existing ultrasound systems.

FIG. 7 illustrates a schematic of a first light pattern 122*a* in accordance with some embodiments. FIG. 8 illustrates a schematic of a second light pattern 122*b* in accordance with some embodiments. Notably, when referring to a generic light pattern herein, the light pattern 122 is referenced. When referring to a specific light pattern herein, the light pattern 122*a*, 122*b*, or the like is referenced.

Figure 6:
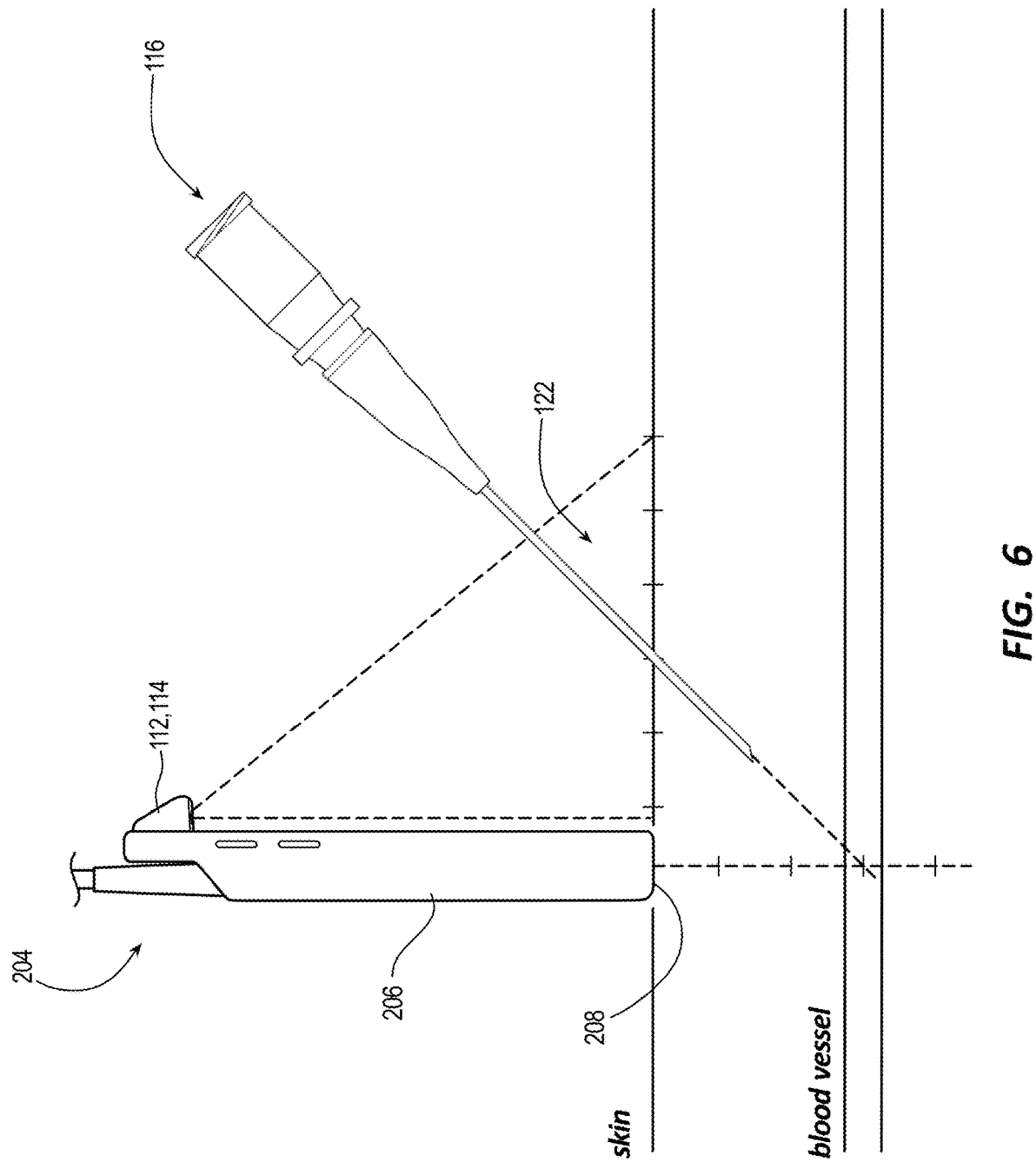
FIG. 6 illustrates a schematic of guided insertion of a needle into an anatomical target with a light pattern projected in a procedural field in accordance with some embodiments.

As shown, the light pattern 122*a* of 122*b* includes periodic hash marks 124 along one or more rays 126 radiating from a central axis of the ultrasound probe 104 in the plane of the probe head 108. Indeed, the light pattern 122*a* includes the hash marks 124 along one ray 126 radiating from the central axis of the ultrasound probe 104, whereas the light pattern 122*b* includes the hash marks 124 along three rays 126 radiating from the central axis of the ultrasound probe 104. As shown in FIG. 6, each hash mark of the hash marks 124 corresponds to a depth under the probe head 108 accessible by the needle 116 along an associated ray 126 at a needle-insertion angle with respect to the plane of the probe head 108.

Figure 9:
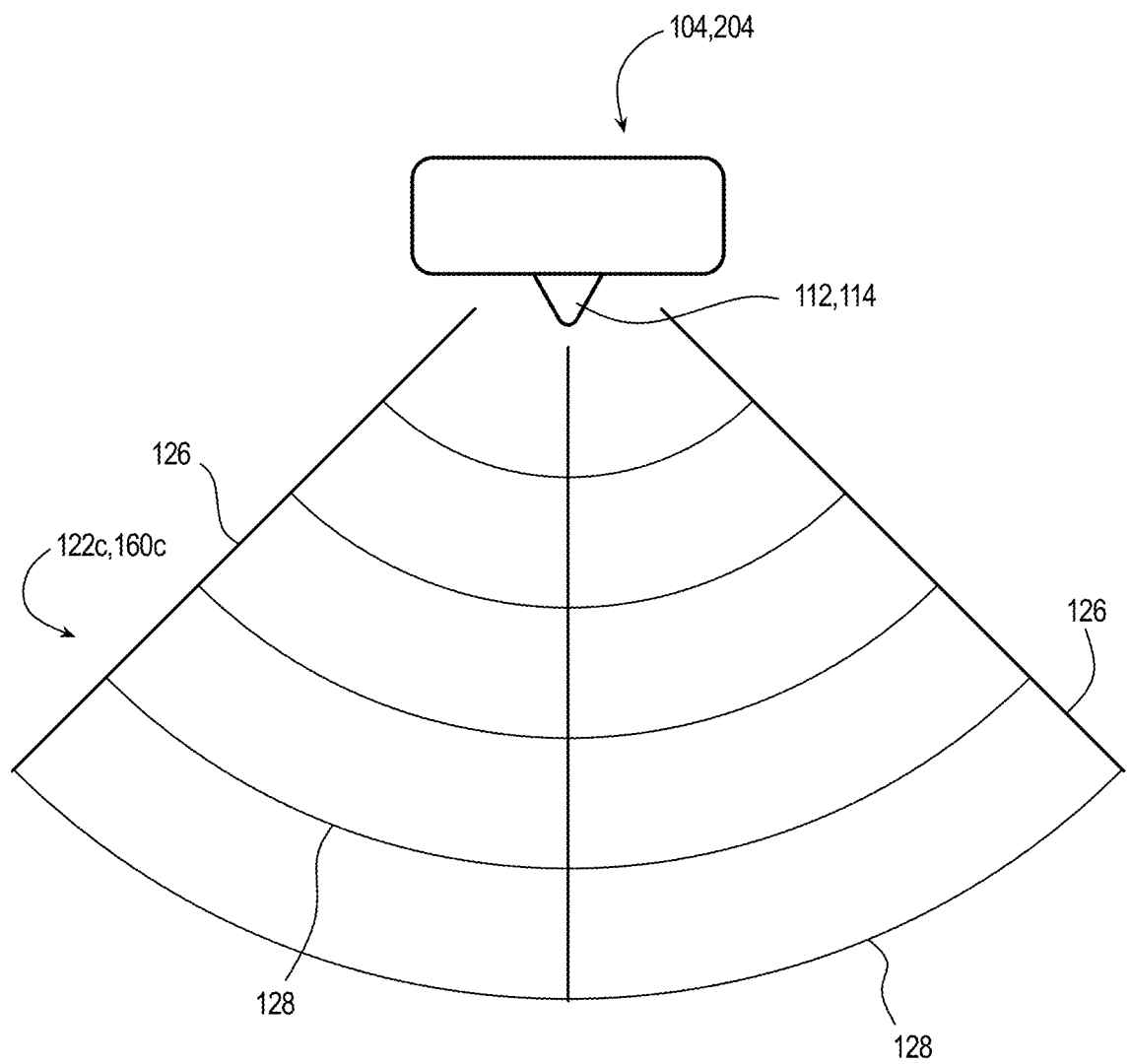
FIG. 9 illustrates a schematic of a third light pattern or a third overlying pattern in accordance with some embodiments.

FIG. 9 illustrates a schematic of a third light pattern 122*c* in accordance with some embodiments.

As shown, the light pattern 122*c* includes periodic concentric circular arcs 128 bound between two or more rays 126 radiating from the central axis of the ultrasound probe 104 in the plane of the probe head 108. Indeed, the light pattern 122*c* includes the circular arcs 128 bound between three rays 126 radiating from the central axis of the ultrasound probe 104. As shown in FIG. 6, each circular arc of the circular arcs 128 corresponds to a depth under the probe head 108 accessible by the needle 116 along an associated ray 126 at a needle-insertion angle with respect to the plane of the probe head 108. Notably, the associated ray 126 can be an intervening ray between the two-or-more rays 126 of the light pattern 122*c* radiating from the central axis of the ultrasound probe 104. The intervening ray need not be a visible ray of the light pattern 122*c*; the intervening ray can be envisioned between the two-or-more rays 126 of the light pattern 122*c* and followed with the needle 116 when establishing an insertion site therewith as set forth in the method below.

The ultrasound probe 104 can also include a needle-guide holder 130 extending from the side of the probe head 108 in common with the side of the ultrasound probe 104 including the camera 112, whether the foregoing side is the major or minor side of the ultrasound probe 104 including the camera 112 or the light-pattern projector 114.

The ultrasound probe 104 can also include a single-use needle guide 132 configured to couple to the needle-guide holder 130. The needle guide 132, the needle-guide holder 130, or a combination of the needle guide 132 and the needle-guide holder 130 can include at least one degree of freedom enabling the needle guide 132 to swivel between sides of the ultrasound probe 104. Indeed, the needle guide 132 can swivel between minor sides of the ultrasound probe 104 if the needle-guide holder 130 extends from a major side of the ultrasound probe 104. The needle guide 132 can alternatively swivel between major sides of the ultrasound probe 104 if the needle-guide holder 130 extends from a minor side of the ultrasound probe 104. To enable the needle guide 132 to swivel between the foregoing sides of the ultrasound probe 104, the needle guide 132 and the needle-guide holder 130 can include a joint (e.g., ball joint) formed therebetween that provides the degree of freedom needed. If the needle guide 132 is used with the needle 116 to establish an insertion site, the needle guide 132 can be advantageously swiveled along each circular arc of the circular arcs 128 of the light pattern 122*c*. The needle 116 can be subsequently inserted along any existing or envisioned ray of the light pattern 122*c* to establish an insertion site.

FIGS. 4 and 5 illustrate different views of the ultrasound probe 204 in accordance with some embodiments.

As shown, the ultrasound probe 204 includes a probe body 206, a probe head 208 extending from a distal end of the probe body 206, and the plurality of ultrasonic transducers 110 arranged in an array in the probe head 208. In addition, the ultrasound probe 204 can include the camera 112 integrated into a side of the ultrasound probe 204, the light-pattern projector 114 integrated into the side of the ultrasound probe 204, or both the camera 112 and the light-pattern projector 114 integrated into the side of the ultrasound probe 204. As such, the ultrasound probe 204 is like the ultrasound probe 104 in certain ways. Therefore, the description set forth above for the ultrasound probe 104 likewise applies to the ultrasound probe 204.

The ultrasound probe 204 also includes a display 134 integrated into the side of the ultrasound probe 204, specifically the top side (or front face) of the ultrasound probe 204, which differentiates the ultrasound probe 204 from the ultrasound probe 104. The display 134 is configured to render ultrasound images 136 on a display screen thereof, which allows a clinician to sustain spatial attention in the procedural field when establishing an insertion site with the needle 116 as set forth in the method below, thereby obviating the clinician from frequently switching his or her spatial attention between the procedural field, which includes the display 134, and another display (e.g., the display 158 of the console 102) as done with existing ultrasound systems. In addition, the display 134 is configured to render one or more overlying needle trajectories 138 over the ultrasound images 136. (See, for example, FIG. 11 for the one-or-more needle trajectories 138.) The one-or-more needle trajectories 138 are configured for guided insertion of the needle 116 into an anatomical target under the probe head 208 on the display 134. Indeed, the one-or-more needle trajectories 138 are in accordance with one or more depths accessible by the needle 116 as indicated by the light pattern 122.

Notably, the ultrasound probe 104 or 204 can include magnetic sensors to enhance guided insertion of the needle 116 into an anatomical target as set forth herein with magnetic-based needle guidance. Such magnetic-based needle guidance is disclosed in U.S. Pat. Nos. 8,388,541; 8,781,555; 8,849,382; 9,456,766; 9,492,097; 9,521,961; 9,554,716; 9,636,031; 9,649,048; 10,449,330; 10,524,691; and 10,751,509, each of which is incorporated by reference in its entirety into this application.

Figure 12:
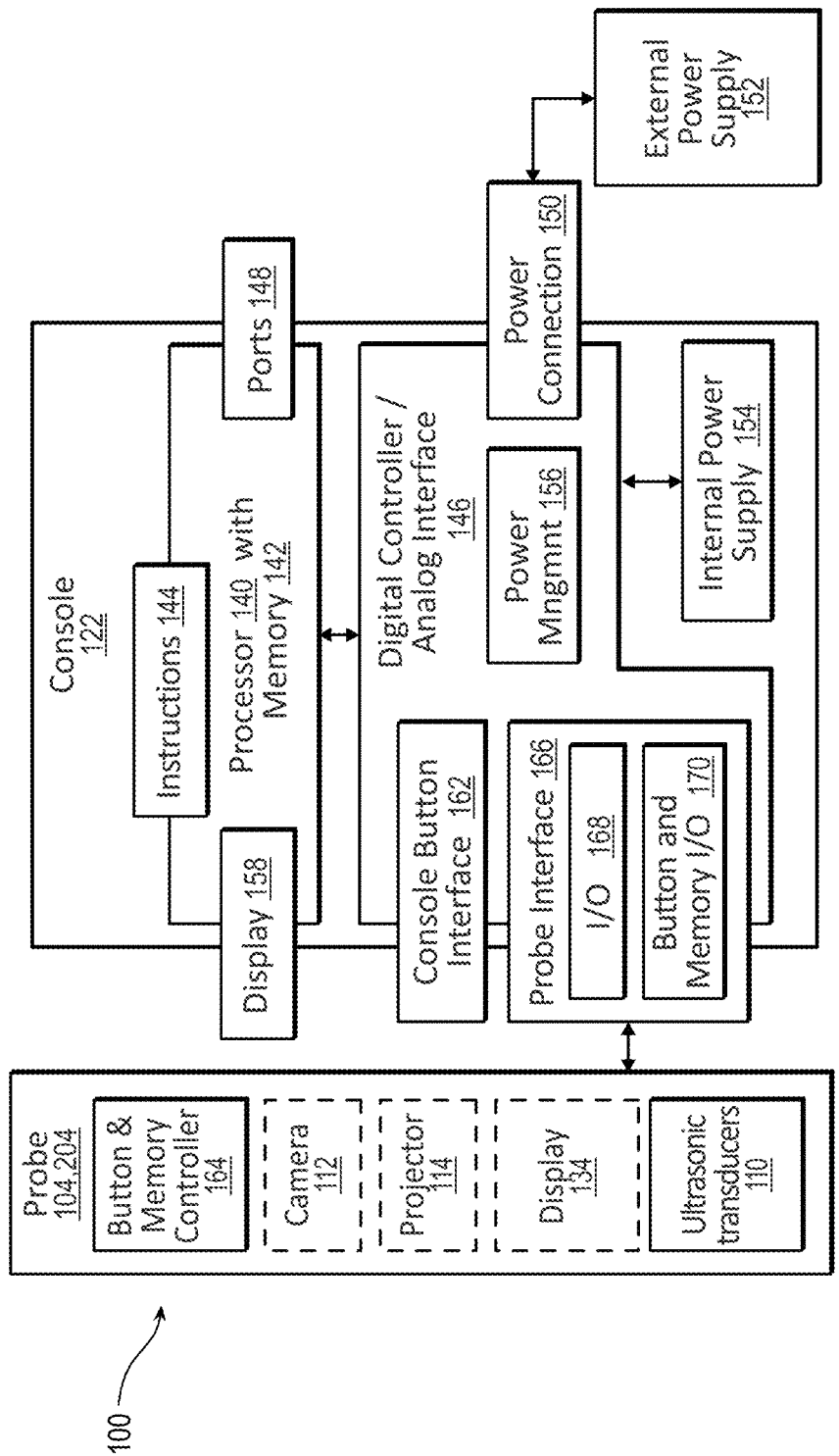
FIG. 12 illustrates a block diagram of the ultrasound system in accordance with some embodiments.

FIG. 12 illustrates a block diagram of the ultrasound system 100 in accordance with some embodiments.

As shown, the console 102 includes a variety of components including a processor 140 and memory 142 such as random-access memory ("RAM") or non-volatile memory (e.g., electrically erasable programmable read-only memory ["EEPROM"]) for controlling various functions of the ultrasound system 100 during operation thereof. Indeed, the console 102 is configured to instantiate by way of executable instructions 144 stored in the memory 142 and executed by the processor 140 various processes for controlling the various functions of the ultrasound system 100.

As to the various processes for controlling the various functions of the ultrasound system 100, the various processes can include beamforming by way of a beamformer configured to drive the ultrasonic transducers 110, wherein driving the ultrasonic transducers 110 includes emitting generated ultrasound signals as well as receiving, amplifying, and digitizing reflected ultrasound signals; signal processing by way of a signal processor configured to detect an amplitude of each of the foregoing reflected ultrasound signals or the digitized signals corresponding thereto; and image processing by way of an image processor configured to manage storage of detected amplitudes and send the ultrasound images 136 corresponding to collections of the detected amplitudes to the display screen of the display 134 or 158 upon completion of the ultrasound images 136.

Further to the various processes for controlling the various functions of the ultrasound system 100, the various processes can include processing electrical signals corresponding to color and brightness data from an image sensor of the camera 112 of the ultrasound probe 104 or 204 into the one-or-more still or moving images 120; determining depths for various anatomical structures in the ultrasound images 136 by way of delays in time between emitting the generated ultrasound signals from the ultrasonic transducers 110 and receiving the reflected ultrasound signals by the ultrasonic transducers 110; adjusting a scale of the light pattern 122 projected from the light-pattern projector 114 in accordance with both the depths for the various anatomical structures in the ultrasound images 136 and a needle-insertion angle, wherein the needle-insertion angle is selected from a single ultrasound system-defined needle-insertion angle, a clinician-selected needle-insertion angle among various ultrasound system-defined needle-insertion angles, and a dynamic needle-insertion angle determined by way of magnetic-based needle guidance; adjusting a scale of the overlying pattern 160 lying over the one-or-more still or moving images 120 in accordance with both the depths for the various anatomical structures in the ultrasound images 136 and the needle-insertion angle; and adjusting a scale of the one-or-more needle trajectories 138 lying over the ultrasound images 136 in accordance with both the depths for various anatomical structures in the ultrasound images 136 and the needle-insertion angle.

The console 102 also includes a digital controller/analog interface 146 in communication with both the processor 140 and other system components to govern interfacing between the ultrasound probe 104 or 204 and the foregoing system components. Ports 148 are also included in the console 102 for connection with additional system components including can be universal serial bus ("USB") ports, though other types of ports can be used for these connections or any other connections shown or described herein.

A power connection 150 is included with the console 102 to enable an operable connection to an external power supply 152. An internal power supply 154 (e.g., a battery) can also be employed either with or exclusive of the external power supply 152. Power management circuitry 156 is included with the digital controller/analog interface 146 of the console 102 to regulate power use and distribution.

A display 158 integrated into the console 102 is configured to render on a display screen thereof a graphical user interface ("GUI"), the ultrasound images 136 attained by the ultrasound probe 104 or 204, the one-or-more still or moving images 120 of the procedural field attained by the camera 112 of the ultrasound probe 104 or 204, an overlying pattern 160 lying over the one-or-more still or moving images 120, the one-or-more needle trajectories 138 lying over the ultrasound images 136, etc. That said, the display 158 can alternatively be separate from the console 102 and communicatively coupled thereto. Regardless, control buttons (see FIGS. 1, 3, 10, and 11) accessed through a console button interface 162 of the console 102 can be used to immediately call up to the display screen a desired mode of the ultrasound system 100 for assisting with an ultrasound-based medical procedure such as that for establishing an insertion site with the needle 116, placing a VAD such as a catheter in a blood vessel of a patient at the insertion site, or the like. For example, a mode of the ultrasound system 100 for establishing an insertion site with the needle 116 can include rendering the one-or-more still or moving images 120 of the procedural field, the overlying pattern 160 lying over the one-or-more still or moving images 120, the one-or-more needle trajectories 138 lying over the ultrasound images 136, or a combination thereof.

Figure 10:
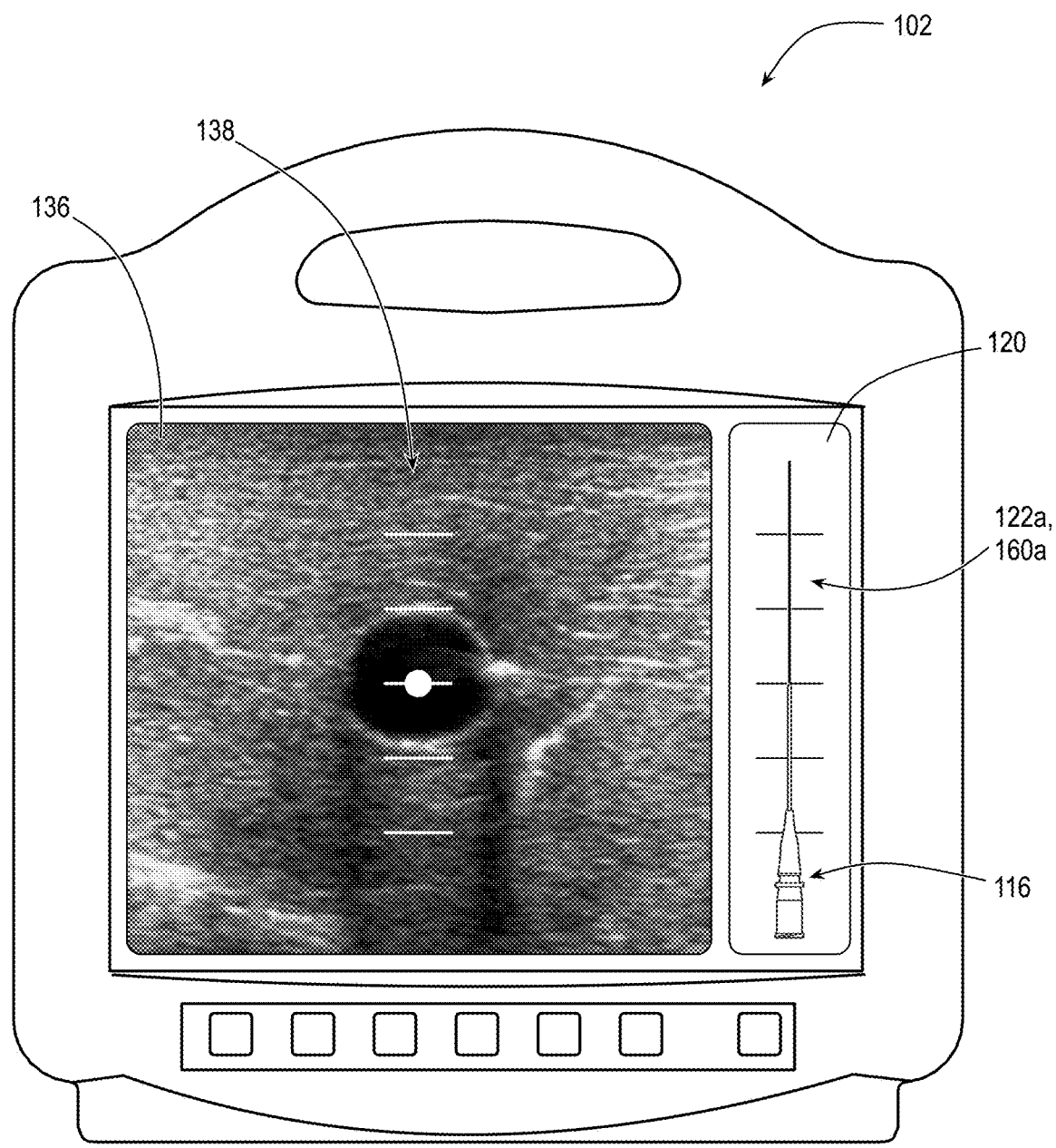
FIG. 10 illustrates guided insertion of a needle into an anatomical target with the first light pattern or the first overlying pattern over one or more still or moving images on a display in accordance with some embodiments.
Figure 11:
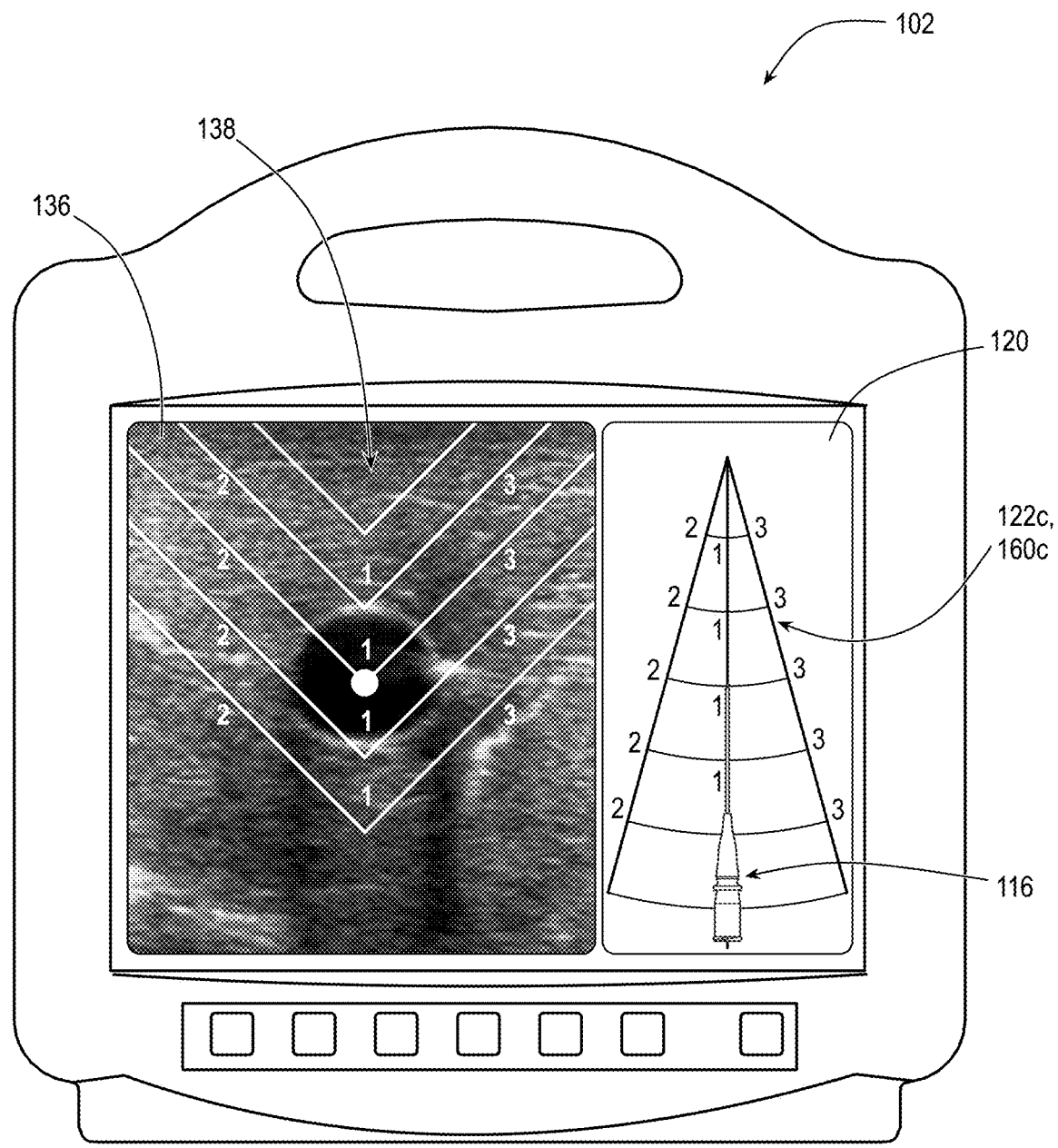
FIG. 11 illustrates guided insertion of a needle into an anatomical target with the third light pattern or the third overlying pattern over the one-or-more still or moving images on the display in accordance with some embodiments.

FIGS. 10 and 11 illustrate guided insertion of the needle 116 into an anatomical target of an ultrasound image with the light pattern 122, specifically the light pattern 122a and 122c, respectively, as shown in the one-or-more still or moving images 120 adjacent the ultrasound image on the display 158.

When rendered on the display screen, the one-or-more still or moving images 120 show at least the needle 116 when the needle 116 is present in the spatial region about the probe head 108 or 208, which, even alone, allows a clinician to sustain spatial attention on the display 158 when establishing an insertion site with the needle 116. If the ultrasound probe 104 or 204 includes the light-pattern projector 114, however, the one-or-more still or moving images 120 can show both the light pattern 122 in the spatial region about the probe head 108 or 208 and the needle 116 in relation to the light pattern 122 for guided insertion of the needle 116 into an anatomical target under the probe head 108 or 208 on the display 158. Having both the light pattern 122 and the needle 116 shown in the one-or-more still or moving images 120 further allows a clinician to sustain spatial attention on the display 158 when establishing the insertion site with the needle 116, thereby obviating the clinician from frequently switching his or her spatial attention between the display 158 and the procedural field as done with existing ultrasound systems.

FIGS. 10 and 11 also illustrate guided insertion of the needle 116 into an anatomical target of an ultrasound image respectively with the overlying pattern 160, specifically the overlying pattern 160a and 160c, respectively, over the one-or-more still or moving images 120 adjacent the ultrasound image on the display 158.

Following on the foregoing, if the ultrasound probe 104 or 204 does not include the light-pattern projector 114, or if a clinician prefers not to use the light-pattern projector 114 of the ultrasound probe 104 or 204, the one-or-more still or moving images 120 can show the overlying pattern 160 lying thereover. When the needle 116 is present in the spatial region about the probe head 108 or 208, the one-or-more still or moving images 120 can thusly show both the overlying pattern 160 and the needle 116 in relation to the overlying pattern 160 for guided insertion of the needle 116 into an anatomical target under the probe head 108 or 208 on the display 158. Having both the overlying pattern 160 and the needle 116 shown in the one-or-more still or moving images 120 further allows a clinician to sustain spatial attention on the display 158 when establishing the insertion site with the needle 116, thereby obviating the clinician from frequently switching his or her spatial attention between the display 158 and the procedural field as done with existing ultrasound systems.

Like the light pattern 122a or 122b, the overlying pattern 160a or 160b includes the periodic hash marks 124 along one or more rays 126 radiating from the central axis of the ultrasound probe 104 or 204 in the plane of the probe head 108 or 208; however, unlike the light pattern 122a or 122b, the hash marks 124 and the one-or-more rays 126 are virtual, existing only on the display screen. By analogy to the light pattern 122a, the overlying pattern 160a likewise includes the hash marks 124 along one ray 126 radiating from the central axis of the ultrasound probe 104 or 204, and, by analogy to the light pattern 122b, the overlying pattern 160b likewise includes the hash marks 124 along three rays 126 radiating from the central axis of the ultrasound probe 104 or 204. Each hash mark of the hash marks 124 corresponds to a depth under the probe head 108 or 208 accessible by the needle 116 along an associated ray 126 at a needle-insertion angle with respect to the plane of the probe head 108 or 208.

Like the light pattern 122c, the overlying pattern 160c includes periodic concentric circular arcs 128 bound between two or more rays 126 radiating from a central axis of the ultrasound probe 104 or 204 in the plane of the probe head 108 or 208; however, unlike the light pattern 122c, the circular arcs 128 and the two-or-more rays 126 are virtual, existing only on the display screen. By analogy to the light pattern 122c, the overlying pattern 160c likewise includes the circular arcs 128 bound between three rays 126 radiating from the central axis of the ultrasound probe 104 or 204. Each circular arc of the circular arcs 128 corresponds to a depth under the probe head 108 or 208 accessible by the needle 116 along an associated ray 126 at a needle-insertion angle with respect to the plane of the probe head 108 or 208. Notably, the associated ray 126 can be an intervening ray between the two-or-more rays 126 of the overlying pattern 160c radiating from the central axis of the ultrasound probe 104 or 204. The intervening ray need not be a visible ray of the overlying pattern 160c; the intervening ray can be envisioned between the two-or-more rays 126 of the overlying pattern 160c and followed with the needle 116 when establishing an insertion site therewith as set forth in the method below.

As set forth above, the display 158 is configured to render on the display screen thereof the one-or-more needle trajectories 138 lying over the ultrasound images 136. The one-or-more needle trajectories 138 are configured for guided insertion of the needle 116 into an anatomical target under the probe head 108 or 208 on the display 158. Indeed, as shown in FIG. 11, the one-or-more needle trajectories 138 are in accordance with one or more depths accessible by the needle 116 indicated by the light pattern 122c or the overlying pattern 160c.

The needle trajectories 138 labeled '1' in FIG. 11 are straightforwardly understood as being in a plane perpendicular to that of an ultrasound beam for a so called out-of-plane view with respect to the needle 116. Moving the needle 116 from circular arc 128 to circular arc 128 of the light pattern 122c or overlying pattern 160c of FIG. 11 toward the central axis of the ultrasound probe 104 or 204 while keeping the needle-insertion angle constant moves the needle 116 from trajectory to trajectory of the one-or-more needle trajectories 138 in a same direction (e.g., up) on the display screen. Indeed, inserting the needle 116 into a patient at the circular arc 128 nearest the central axis of the ultrasound probe 104 or 204 results in overshooting an anatomical target, for example, a blood vessel under the probe head 108 or 208. Notably, the needle 116 could still access the blood vessel but distal of the probe head 108 or 208. Similarly, moving the needle 116 from circular arc 128 to circular arc 128 of the light pattern 122c or overlying pattern 160c of FIG. 11 away from the central axis of the ultrasound probe 104 or 204 while keeping the needle-insertion angle constant moves the needle 116 from trajectory to trajectory of the one-or-more needle trajectories 138 in a same direction (e.g., down) on the display screen. Indeed, inserting the needle 116 into the patient at the circular arc 128 farthest from the central axis of the ultrasound probe 104 or 204 results in undershooting the blood vessel under the probe head 108 or 208. Notably, the needle 116 would still access the blood vessel but proximal of the probe head 108 or 208 and, ultimately, through a backwall of the blood vessel if the needle trajectory is completely followed.

The needle trajectories 138 labeled '2' and '3' in of FIG. 11 are in mirrored planes oblique to that of the ultrasound beam, and, as such, approach the blood vessel obliquely. However, like that set forth for the needle trajectories 138 labeled '1' in FIG. 11, moving the needle 116 from circular arc 128 to circular arc 128 of the light pattern 122c or overlying pattern 160c of FIG. 11 toward the central axis of the ultrasound probe 104 or 204 while keeping the needle-insertion angle constant moves the needle 116 from trajectory to trajectory of the one-or-more needle trajectories 138 in a same direction (e.g., up) on the display screen. Moving the needle 116 from circular arc 128 to circular arc 128 of the light pattern 122c or overlying pattern 160c of FIG. 11 away from the central axis of the ultrasound probe 104 or 204 while keeping the needle-insertion angle constant moves the needle 116 from trajectory to trajectory of the one-or-more needle trajectories 138 in a same direction (e.g., down) on the display screen.

Adverting briefly back to the ultrasound probe 104 or 204, the ultrasound probe 104 or 204 includes the buttons 118 for operating the ultrasound probe 104 or 204 or the ultrasound system 100 of which the ultrasound probe 104 or 204 is part. For example, the buttons 118 can be configured for selecting a desired mode of the ultrasound system 100 as set forth above. The ultrasound probe 104 or 204 includes a button-and-memory controller 164 configured for operable communication with a probe interface 166 of the console 102, which probe interface 166 includes an input/output ("I/O") component 168 for interfacing with the ultrasonic transducers 110 and a button-and-memory I/O component 170 for interfacing with the button-and-memory controller 164.

Methods

Methods include a method of using the ultrasound system 100 to establish an insertion site for access to an anatomical structure (e.g., blood vessel) of a patient. The method includes one or more steps selected from an ultrasound probe-obtaining step, an ultrasound probe-moving step, a recording step, an ultrasound image-monitoring step, a needle guide-attaching step, a needle guide-swiveling step, and a needle-inserting step.

The ultrasound probe-obtaining step includes obtaining the ultrasound probe 104. As set forth above, the ultrasound probe 104 includes the probe body 106, the probe head 108 extending from the distal end of the probe body 106, and the camera 112 integrated into the side of the ultrasound probe 104.

The needle guide-attaching step includes attaching the needle guide 132 to the needle-guide holder 130 extending from the probe body 106. The needle guide 132 includes a needle through hole configured to direct the needle 116 into the patient under the probe head 108 at the needle-insertion angle defined by the needle guide 132.

The ultrasound probe-moving step includes moving the ultrasound probe 104 over the patient while the ultrasound probe 104 emits generated ultrasound signals into the patient from the ultrasonic transducers 110 in the probe head 108 and receives reflected ultrasound signals from the patient by the ultrasonic transducers 110.

The recording step includes recording the one-or-more still or moving images 120 of the procedural field including a subject portion of the patient therein. As set forth above, the one-or-more still or moving images 120 are recorded with a depth of field including the plane of the distal end of the probe head 108 and the field of view including the spatial region about the probe head 108.

The ultrasound image-monitoring step includes monitoring ultrasound images 136 rendered on the display screen of the display 158 associated with the console 102 of the ultrasound system 100 to identify an anatomical target of the patient under the probe head 108.

The needle guide-swiveling step includes swiveling the needle guide 132 between sides of the ultrasound probe 104 to find a suitable needle trajectory before the needle-inserting step. The needle-guide holder 130, the needle guide 132, or a combination of the needle-guide holder 130 and the needle guide 132 such as the joint formed therebetween includes at least one degree of freedom enabling the swiveling of the needle guide 132.

The needle-inserting step includes inserting the needle 116 into the anatomical target. The inserting of the needle 116 into the anatomical target during the needle-inserting step is guided in the procedural field with reference to the light pattern 122 in the spatial region about the probe head 108, on the display 158 with reference to the one-or-more still or moving images 120 or the one-or-more needle trajectories 138 rendered on the display screen thereof, or a combination thereof.

As to guidance in the procedural field with reference to the light pattern 122, the light pattern 122 is projected into the spatial region about the probe head 108 from the light-pattern projector 114 and focused in the plane of the distal end of the probe head 108 for guiding the needle 116 in the procedural field. As set forth above, the light pattern 122a or 122b includes the periodic hash marks 124 along the one-or-more rays 126 radiating from the central axis of the ultrasound probe 104 in the plane of the probe head 108. Each hash mark of the hash marks 124 corresponds to a depth under the probe head 108 accessible by the needle 116 along an associated ray 126 at a needle-insertion angle with respect to the plane of the probe head 108. As further set forth above, the light pattern 122c includes the periodic concentric circular arcs 128 bound between the two-or-more rays 126 radiating from the central axis of the ultrasound probe 104 in the plane of the probe head 108. Each circular arc of the circular arcs 128 corresponds to a depth under the probe head 108 accessible by the needle 116 along an associated ray 126 at a needle-insertion angle with respect to the plane of the probe head 108.

As to guidance on the display 158 with reference to the one-or-more still or moving images 120, the one-or-more still or moving images 120 can show both the light pattern 122 in the spatial region about the probe head 108 and the needle 116 in relation to the light pattern 122 for guiding the needle 116 on the display 158. However, if the ultrasound probe 104 does not include the light-pattern projector 114, or if a clinician prefers not to use the light-pattern projector 114 of the ultrasound probe 104, the one-or-more still or moving images 120 can show the overlying pattern 160 lying thereover for guiding the needle 116 on the display 158. As set forth above, the overlying pattern 160a or 160b includes the periodic hash marks 124 along the one-or-more rays 126 radiating from the central axis of the ultrasound probe 1014 in the plane of the probe head 108. Each hash mark of the hash marks 124 corresponds to a depth under the probe head 108 accessible by the needle 116 along an associated ray 126 at a needle-insertion angle with respect to the plane of the probe head 108. As further set forth above, the overlying pattern 160c includes the periodic concentric circular arcs 128 bound between the two-or-more rays 126 radiating from the central axis of the ultrasound probe 104 in the plane of the probe head 108. Each circular arc of the circular arcs 128 corresponds to a depth under the probe head 108 accessible by the needle 116 along an associated ray 126 at a needle-insertion angle with respect to the plane of the probe head 108.

Further as to guidance on the display 158 with reference to the one-or-more needle trajectories 138, the ultrasound images 136 can show the one-or-more needle trajectories 138 in accordance with one or more depths accessible by the needle 116 indicated by the light pattern 122 or overlying pattern 160 in the one-or-more still or moving images 120 for guiding the needle 116 on the display 158.

Notably, the foregoing method involves the ultrasound probe 104; however, the method can be modified for the ultrasound probe 204. In such a method, the ultrasound images 136 are displayed on the display 134 of the ultrasound probe 204, optionally, in combination with the ultrasound images 136 and the one-or-more still or moving images 120 on the display 158 of the console 102. As set forth above, displaying the images on the display 134 of the ultrasound probe 204 allows a clinician to sustain spatial attention in the procedural field when establishing the insertion site with the needle 116 in the needle-inserting step, thereby obviating the clinician from frequently switching his or her spatial attention between the procedural field, which includes the display 134, and another display (e.g., the display 158 of the console 102) as done with existing ultrasound systems.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. An ultrasound probe, comprising:
   a probe body;
   a probe head extending from a distal end of the probe body, the probe head including a plurality of ultrasonic transducers arranged in an array;
   a camera integrated into a side of the ultrasound probe, the camera configured for recording one or more still or moving images of a procedural field with a depth of field including a plane of a distal end of the probe head and a field of view including a spatial region about the probe head; and
   a light-pattern projector integrated into the side of the ultrasound probe adjacent to the camera, the light-pattern projector configured to project a light pattern in the spatial region about the probe head focused in the plane of the distal end of the probe head for guided insertion of a needle into an anatomical target under the probe head in the procedural field, the light pattern including periodic hash marks along one or more rays radiating from a central axis of the ultrasound probe in the plane of the probe head, and each hash mark of the periodic hash marks corresponding to a depth under the probe head accessible by the needle along an associated ray at a needle-insertion angle with respect to the plane of the probe head.

2. The ultrasound probe of claim 1, further comprising a needle-guide holder extending from a side of the probe head in common with the side of the ultrasound probe including the camera.

3. The ultrasound probe of claim 2, further comprising a single-use needle guide coupled to the needle-guide holder, wherein the needle-guide holder, the single-use needle guide, or a combination of the needle-guide holder and the single-use needle guide includes at least one degree of freedom enabling the needle guide to swivel between sides of the ultrasound probe.

4. An ultrasound system, comprising:
an ultrasound probe including:
    a probe body;
    a probe head extending from a distal end of the probe body, the probe head including a plurality of ultrasonic transducers arranged in an array;
    a camera integrated into a side of the ultrasound probe, the camera configured for recording one or more still or moving images of a procedural field with a depth of field including a plane of a distal end of the probe head and a field of view including a spatial region about the probe head; and
    a light-pattern projector integrated into the side of the ultrasound probe adjacent to the camera, the light-pattern projector configured to project a light pattern in the spatial region about the probe head focused in the plane of the distal end of the probe head for guided insertion of a needle into an anatomical target under the probe head in the procedural field; and
a console including a display configured to render on a display screen thereof:
    ultrasound images and the one or more still or moving images of the procedural field; and
    one or more overlying needle trajectories in accordance with one or more depths accessible by the needle indicated by the light pattern, the one or more overlying needle trajectories lying over the ultrasound images for the guided insertion of the needle into the anatomical target under the probe head on the display.

5. The ultrasound system of claim 4, the ultrasound probe further comprising a needle-guide holder extending from a side of the probe head in common with the side of the ultrasound probe including the camera.

6. The ultrasound system of claim 5, further comprising a single-use needle guide coupled to the needle-guide holder, the needle-guide holder, the single-use needle guide, or a combination of the needle-guide holder and the single-use needle guide including at least one degree of freedom enabling the single-use needle guide to swivel between sides of the ultrasound probe.

7. The ultrasound system of claim 4, wherein the light pattern includes periodic hash marks along one or more rays radiating from a central axis of the ultrasound probe in the plane of the probe head, each periodic hash mark of the hash marks corresponding to a depth under the probe head accessible by the needle along an associated ray at a needle-insertion angle with respect to the plane of the probe head.

8. The ultrasound system of claim 4, wherein the light pattern includes periodic concentric circular arcs bound between two or more rays radiating from a central axis of the ultrasound probe in the plane of the probe head, each circular arc of the periodic concentric circular arcs corresponding to a depth under the probe head accessible by the needle along an associated ray at a needle-insertion angle with respect to the plane of the probe head.

9. The ultrasound system of claim 4, wherein the one or more still or moving images show both the light pattern in the spatial region about the probe head and the needle in relation to the light pattern, when both the light pattern and the needle are present in the spatial region about the probe head, for the guided insertion of the needle into the anatomical target under the probe head on the display.

10. The ultrasound system of claim 4, wherein the display is further configured to render on the display screen an overlying pattern lying over the one or more still or moving images for guided insertion of the needle into the anatomical target under the probe head on the display.

11. The ultrasound system of claim 10, wherein the overlying pattern includes periodic hash marks along one or more rays radiating from a central axis of the ultrasound probe in the plane of the probe head, each hash mark of the periodic hash marks corresponding to a depth under the probe head accessible by the needle along an associated ray at a needle-insertion angle with respect to the plane of the probe head.

12. The ultrasound system of claim 10, wherein the overlying pattern includes periodic concentric circular arcs bound between two or more rays radiating from a central axis of the ultrasound probe in the plane of the probe head, each circular arc of the periodic concentric circular arcs corresponding to a depth under the probe head accessible by the needle along an associated ray at a needle-insertion angle with respect to the plane of the probe head.

13. The ultrasound system of claim 10, wherein the one or more still or moving images show the needle in relation to the overlying pattern, when the needle is present in the spatial region about the probe head, for the guided insertion of the needle into the anatomical target under the probe head on the display.

14. The ultrasound system of claim 10, wherein the one or more overlying needle trajectories are also in accordance with the one or more depths accessible by the needle indicated by the overlying pattern.

15. An ultrasound probe, comprising:
a probe body;
a probe head extending from a distal end of the probe body, the probe head including a plurality of ultrasonic transducers arranged in an array;
a camera integrated into a side of the ultrasound probe, the camera configured for recording one or more still or moving images of a procedural field with a depth of field including a plane of a distal end of the probe head and a field of view including a spatial region about the probe head; and
a light-pattern projector integrated into the side of the ultrasound probe adjacent to the camera, the light-pattern projector configured to project a light pattern in the spatial region about the probe head focused in the plane of the distal end of the probe head for guided insertion of a needle into an anatomical target under the probe head in the procedural field, the light pattern including periodic concentric circular arcs bound between two or more rays radiating from a central axis of the ultrasound probe in the plane of the probe head, and each circular arc of the periodic concentric circular arcs corresponding to a depth under the probe head accessible by the needle along an associated ray at a needle-insertion angle with respect to the plane of the probe head.

16. The ultrasound probe of claim 15, further comprising a needle-guide holder extending from a side of the probe head in common with the side of the ultrasound probe including the camera.

17. The ultrasound probe of claim 16, further comprising a single-use needle guide coupled to the needle-guide holder, wherein the needle-guide holder, the single-use needle guide, or a combination of the needle-guide holder and the single-use needle guide includes at least one degree of freedom enabling the single-use needle guide to swivel between sides of the ultrasound probe.

* * * * *